(12) United States Patent
Nussbaum

(10) Patent No.: US 9,772,330 B2
(45) Date of Patent: Sep. 26, 2017

(54) NUCLEIC ACID APTAMER-BASED DIAGNOSTIC METHODS WITH NOVEL TECHNIQUES FOR SIGNAL ENHANCEMENT

(71) Applicant: APTATECK BIO LTD., Ness Ziona (IL)

(72) Inventor: Ofer Nussbaum, Rehovot (IL)

(73) Assignee: APTATECK BIO LTD., Rehovot (IL)

( * ) Notice: Subject to any disclaimer, the term of this patent is extended or adjusted under 35 U.S.C. 154(b) by 0 days.

(21) Appl. No.: 14/565,759

(22) Filed: Dec. 10, 2014

(65) Prior Publication Data

US 2015/0160207 A1 Jun. 11, 2015

Related U.S. Application Data

(62) Division of application No. 13/808,502, filed as application No. PCT/IL2011/000530 on Jul. 6, 2011, now abandoned.

(60) Provisional application No. 61/361,611, filed on Jul. 6, 2010.

(51) Int. Cl.
*G01N 33/50* (2006.01)
*G01N 33/543* (2006.01)
*C12N 15/115* (2010.01)
*C12Q 1/68* (2006.01)
*C12Q 1/70* (2006.01)

(52) U.S. Cl.
CPC ..... *G01N 33/54393* (2013.01); *C12N 15/115* (2013.01); *C12Q 1/6816* (2013.01); *C12Q 1/6825* (2013.01); *C12Q 1/6876* (2013.01); *C12Q 1/706* (2013.01); *G01N 33/54306* (2013.01); *C12N 2310/16* (2013.01); *C12N 2320/10* (2013.01); *G01N 2333/49* (2013.01); *G01N 2333/585* (2013.01); *G01N 2469/10* (2013.01)

(58) Field of Classification Search
None
See application file for complete search history.

(56) References Cited

U.S. PATENT DOCUMENTS

| | | | |
|---|---|---|---|
| 3,951,748 A * | 4/1976 | Devlin | A61K 39/44 435/28 |
| 5,925,533 A | 7/1999 | Doth et al. | 435/7.94 |
| 6,458,543 B1 | 10/2002 | Gold et al. | |
| 2009/0203028 A1 | 8/2009 | Yamamoto | |

FOREIGN PATENT DOCUMENTS

| | | |
|---|---|---|
| WO | 0179562 A1 | 10/2001 |
| WO | 2005113817 A2 | 12/2005 |
| WO | 2007024676 A2 | 3/2007 |
| WO | 2007117444 A2 | 10/2007 |
| WO | 2009070640 A2 | 6/2009 |

OTHER PUBLICATIONS

Zeeshan M, et al. "Comparison of different phenotypic methods of detection of methicillin resistance in *Staphylococcus aureus* with the molecular detection of mec-a gene" J. Coll. Physicians. Surg. Pak. 17:666-70 (2007).
Edmonds, M. "Branched RNA" BioEssays. 6:212-216 (1987).
Lin (I) (Clinical Chemistry 2009 vol. 55, p. 1686-1693).
Goddard et al. (Prog Polym Sci 2007 vol. 32, p. 698-725).
Lisa R. Paborsky et al. "The Single-stranded DNA Aptamer-binding Site of Human Thrombin" The Journal of Biological Chemistry. 268:20606-20811 (1993).
Mandona Sassanfar, Jack W. Szostak. "An RNA motif that binds ATP" Letters to Nature. 364:550-553 (1993).
Monica Mir, Ioanis Katakis. "Aptamers as elements of bioelectronic devices" The Royal Society of Chemistry. 3:620-622 (2007).
Matthew Levy et al. "Quantum-Dot Aptamer Beacons for the Detection of Proteins" ChemBioChem. 6:2163-2166 (2005).
Williams James. "Aptamers" Encyclopedia of Analytical Chemistry. 4848-4871 (2000).
Supriya S. Pai, Andrew D. Ellington. "Using RNA Aptamers and the Proximity Ligation Assay for the Detection of Cell Surface Antigens" Methods in Molecular Biology: Biosensors and Biodetection. 504:385-398 (2009).
Sara Tombelli et al. "Aptamers-based assays for diagnostics, environmental and food analysis" Biomolecular Engineering. 24:191-200 (2007).
Michael J. Whitcombe et al. "The Rational Development of Molecularly Imprinted Polymer-Based Sensors for Protein Detection" Chemical Society Reviews 40:1547-1571 (2011).
Raymond U. Osarogiagbon et al. "CMV Antigenemia Following Bone Marrow Transplantation: Risk Factors and Outcomes" American Society for Blood and Marrow Transplantation. 280-288 (2000).
Violette B. Paragas et al. "The ELF-97 Alkaline Phosphatase Substrate Provides a Bright, Photostable, Fluorescent Signal Amplification Method for FISH" The Journal of Histochemistry and Cytochemistry. 45:3:345-357 (1997).
H M Kerstens et al. "A novel in situ hybridization signal amplification method based on the deposition of biotinylated tyramine" Journal of Histochemistry and Cytochemistry. 43:4: 347-352 (1995).
Mary Edmonds. "Branched RNA" BioEssays. 6;5: 212-216.

(Continued)

*Primary Examiner* — Jacob Cheu
(74) *Attorney, Agent, or Firm* — Browdy and Neimark, PLLC

(57) ABSTRACT

The present invention concerns methods for the detection f target molecules in a sample including several steps of signal amplification allowing the detection of a very low number of target molecules in the tested sample. The detection assay is based on the use of a universal probe which enables the signal amplification. The specific recognition of the target molecule is achieved by using a specific binding agent, preferably an aptamer. The invention further concerns kits and methods for the diagnosis of pathological conditions.

15 Claims, 13 Drawing Sheets

(56) References Cited

OTHER PUBLICATIONS

Tao Chen et al. "Evaluation of Quantitative PCR and Branched-Chain DNA Assay for Detection of Hepatitis B virus DNA in Sera from Hepatocellular Carcinoma and Liver Transplant Patients" Journal of Clinical Microbiology. 38:5:1977-1980 (2000).
P. Maruna et al. "Physiology and Genetics of Procalcitonin" Physiology Research. 49: S57-S61 (2000).
Paresh Dandona et al. "Porcalcitonin Increase after Endotoxin Injection in Normal Subjects" 79:5:1605-1608 (1994).
Chien-Hung Chen. "Quantitative detection of hepatitis B virus DNA in human sera by branched-DNA signal amplification" Journal of Virological Methods. 53:131-137 (1995).
Peter Birner et al. "Signal-Amplified Colorimetric In Situ Hybridization for Assessment of Human Papillomavirus Infection in Cervical Lesions" Modern Pathology 14:7:702-709 (2001).
Hilla Giladi et al. "Small Interfering RNA Inhibits Hepatitis B Virus Replication in Mice" Molecular Therapy 8:5:769-776 (2003).
Lorena Pardo et al. "Characteristics of Community-Associated Methicillin-Resistant *Staphylococcus aureus* (CA-MRSA) Strains Isolated from Skin and Soft-Tissue Infections in Uruguay" International Journal of Microbiology 2009:472126:1-5 (2009).
Yuan-Yuan Li "Ultrasensitive Densitometry Detection of Cytokines with Nanoparticle-Modified Aptamers" Clinical Chemistry 53:6:1061-1066 (2007).
Yong Huang "Electrochemical immunosensor of platelet-derived growth factor with aptamer-prmed polymerase amplification" Analytical Biochemistry 382:16-22 (2008).
Jun Wang et al. "In vitro selection of novel RNA ligands that bind human cytomegalovirus and block viral infection" Program in Infectious Diseases and Immunity 6:571-583 (2000).
Dianah Barrett et al. "Kinetic Characterization of the Glycosyltransferase Module of *Staphylococcus aureus* PBP2" Journal of Bacteriology 187:6:2215-2217 (2005).
Anna Farra et al. "Role of outer membrane protein OprD and penicillin-binding proteins in resistance of Pseudomonas aeruginosa to imipenem and meropenem" International Journal of Antimicrobial Agents 31:427-433 (2008).
Monika Olempska et al. "Detection of tumor stem cell markers in pancreatic carcinoma cell lines" Hepatobiliary and Pancreatic Diseases International.6:1:92-97 (2007).
Ulla Balslev et al. "An Outbreak of Borderline Oxacillin-Resistant *Staphylococcus aureus* (BORSA) in a Dermatological Unit" Microbial Drug Resistance 11:1:78-81 (2005).
Thierry Delair et al. "Synthesis and Characterization of Nucleic Acid-(Co) Polymer Conjugates: Application to Diagnostics." Polymers for Advanced Technologies 9:349-361 (1998).
Julien Bernard et al. "Water-Soluble Dendrigrafts Bearing Saccharidic Moieties: Elaboration and Application to Enzyme Linked OligoSorbent Assay (ELOSA) Diagnostic Tests" Bioconjugate Chemistry 17:6-14 (2006).

* cited by examiner

NUCLEIC ACID APTAMER-BASED DIAGNOSTIC METHODS WITH NOVEL TECHNIQUES FOR SIGNAL ENHANCEMENT

FIELD OF THE INVENTION

This invention relates to diagnostic methods and kits. In particular, the present invention provides novel techniques for enhanced detection and quantitation of target molecules based on a universal detection probe.

BACKGROUND OF THE INVENTION

There is an increasing need for accurate, fast and low cost assays in the fields of in-vitro diagnostics (IVD) and especially in the field of Point of Care (POC) diagnostics. Nucleic Acid aptamers have been considered in recent years for use in diagnostic applications.

Aptamers are oligonucleic acid molecules which are obtained by in vitro selection methods such as Synthetic Evolution of Ligands by Exponential Enrichment (SELEX).

Aptamers have a specific binding to a target molecule such as a protein with high affinities in the nanomolar and subnanomolar range. For example, aptamers against vascular endothelial growth factor and keratinocyte growth factor show affinities of 100 pM and of 1 pM, respectively (L R Paborsky et al., "*The Single-Stranded DNA Aptamer-Binding Site of Human Thrombin*" J. of Biol. Chem. 268 (1993): 808-811). In addition, aptamers can bind small molecules like ATP (M Sassanfar and J W Szostak, "*An RNA Motif That Binds ATP*" Nature 364 (1993): 550-553).

In recent years, aptamers have been studied as therapeutic tools both for treatment and for prevention, with the first aptamer-based drug recently approved by the U.S. FDA in treatment for age-related macular degeneration (AMD).

Several aptamer-based biodetection approaches have been reported in which aptamers were labeled with molecules such as redox probes, fluorescent dyes, or nanocrystals as an integral part of signal transduction (Mir M, and Katakis I. *Aptamers as elements of bioelectronic devices*. Mol. Biosyst. 3 (2007): 620-622; Levy, M; Cater, S F; Ellington, A D. *Quantum-dot aptamer beacons for the detection of proteins*. Chembiochem. 6 (2005):2163-2166). In addition, researchers have recently taken advantage of PCR to amplify DNA aptamers for sensitive detection of protein targets.

In addition, in the past several years there was a growing use of aptamers as chemical antibodies (William James. Aptamers. In Encyclopedia of Analytical Chemistry. R. A. Meyers (2000) 4848-4871 Ó John Wiley & Sons Ltd; Pai S S, Ellington A D, *Using RNA aptamers and the proximity ligation assay for the detection of cell surface antigens*. Methods Mol. Biol. 504 (2009): 385-398).

Patent application, U.S. Pat. No. 6,458,543 describes a nucleic acid ligand "biochip", consisting of a solid support to which one or more specific nucleic acid ligand is attached in a spatially defined manner, enabling the specific binding to a target molecule, if present, in a test mixture.

WO 2007/117444 describes methods for diagnosing and staging diseases by detecting and/or measuring proteins associated with certain clinical conditions using a plurality of aptamers that recognize oligopeptide epitopes on a target protein.

WO 01/79562 describes a novel aptamer based two-site binding sandwich assay, employing nucleic acid ligands as capture and/or reporter molecules.

Mir and Katakis (Mir M, and Katakis I. *Aptamers as elements of bioelectronic devices*. Mol. Biosyst. 3 (2007): 620-622) describe an aptamer based-assay having sensitivity of detection in the range of $10^6$-$10^{12}$ molecules.

SUMMARY OF THE INVENTION

The present invention is based on the development of a detection assay which includes several steps of signal amplification allowing the detection of a very low number of target molecules in a tested sample. The detection assay is based on the use of a universal probe which enables signal amplification. The specific recognition of the target molecule is achieved by using a specific binding agent, preferably but not limited to an aptamer. Using the methods disclosed herein the universal probe is attached to the specific biding agent and largely amplifies the detection signal.

Accordingly, by a first of its aspects, the present invention provides a method for the detection of a target molecule in a sample comprising:

a. obtaining at least one aptamer capable of binding to said target molecule, wherein said at least one aptamer is bound to a matrix;

b. incubating said at least one aptamer which is bound to the matrix with the sample under conditions allowing the binding of the aptamer to the target molecule; thereby forming a matrix-aptamer-target molecule complex;

c. contacting the matrix-aptamer-target molecule complex formed in step (b) with a polymer associated with a member of an affinity couple wherein said polymer further comprising a reactive group; thereby forming a matrix-aptamer-target molecule-polymer complex; and d. contacting said matrix-aptamer-target molecule-polymer complex with a complementary member of said member of an affinity couple, wherein said complementary member is associated with a detectable moiety, wherein the amount of said detectable moiety is indicative of the presence of said target molecule in the sample.

In another aspect, the present invention provides a method for the detection of a target molecule in a sample comprising:

a. obtaining at least one aptamer capable of binding to said target molecule, wherein said at least one aptamer is bound to a matrix;

b. incubating said at least one aptamer which is bound to the matrix with the sample under conditions allowing the binding of the aptamer to the target molecule; thereby forming a matrix-aptamer-target molecule complex;

c. contacting the matrix-aptamer-target molecule complex formed in step (b) with a nucleic acid molecule comprising a reactive group and further comprising a polymerase promoter sequence, thereby forming a matrix-aptamer-target molecule-nucleic acid molecule complex;

d. adding a DNA or RNA polymerase enzyme and nucleotides associated with a member of an affinity couple under suitable conditions to affect DNA or RNA polymerization, thereby obtaining DNA or RNA molecules associated with a member of an affinity couple, and e. contacting said DNA or RNA molecules associated with a member of an affinity couple with a complementary member of said member of an affinity couple associated with a detectable moiety;

wherein the amount of said detectable moiety is indicative of the presence of said target molecule in the sample.

In another aspect, the present invention provides a method for the detection of a target molecule in a sample comprising:

a. obtaining at least one first binding agent capable of binding to said target molecule, wherein said first binding agent is bound to a matrix;

b. incubating said at least one first binding agent which is bound to the matrix with the sample under conditions allowing the binding of the binding agent to the target molecule; thereby forming a matrix-binding agent-target molecule complex;

c. contacting the matrix-binding agent-target molecule complex formed in step (b) with a second binding agent-polymer complex, wherein said second binding agent-polymer complex is obtained by either
  i. obtaining at least one biotinylated second binding agent;
  ii. incubating said at least one biotinylated second binding agent with streptavidin thereby a biotinylated second binding agent streptavidin (b-binding agent-SA) complex is formed; and
  iii. incubating said b-binding agent-SA complex formed in step (ii) with a polymer associated with a member of an affinity couple wherein said polymer further having a reactive group thereby forming a second binding agent-polymer complex; or
  iv. obtaining at least one second binding agent, wherein said at least one second binding agent comprises a reactive group; and
  v. incubating said at least one second binding agent comprising a reactive group with a polymer associated with a member of an affinity couple wherein said polymer further having a reactive group thereby forming a second binding agent-polymer complex;

d. contacting the matrix-binding agent-target molecule complex formed in step (b) with the second binding agent-polymer complex formed in step (c), under conditions allowing the binding of the second binding agent to the target molecule, thereby forming a target molecule-polymer complex;

e. contacting said target molecule-polymer complex formed in step (d) with a complementary member of said member of an affinity couple associated with a detectable moiety, wherein the amount of said detectable moiety is indicative of the presence of said target molecule in the sample.

In another aspect, the present invention provides a method for the detection of a target molecule in a sample comprising:

a. obtaining at least one first binding agent capable of binding to said target molecule, wherein said first binding agent is bound to a matrix;

b. incubating said at least one first binding agent which is bound to the matrix with the sample under conditions allowing the binding of the binding agent to the target molecule; thereby forming a matrix-binding agent-target molecule complex;

c. contacting the matrix-binding agent-target molecule complex formed in step (b) with a second binding agent-nucleic acid complex, wherein said second binding agent-nucleic acid complex is obtained by either
  i. obtaining at least one biotinylated second binding agent;
  ii. incubating said at least one biotinylated second binding agent with streptavidin thereby a biotinylated second binding agent streptavidin (b-binding agent-SA) complex is formed; and
  iii. incubating said b-binding agent-SA complex formed in step (ii) with a nucleic acid having an active group and further comprising a polymerase promoter sequence thereby forming second binding agent-nucleic acid complex; or
  iv. obtaining at least one second binding agent, wherein said at least one second binding agent comprises a reactive group; and
  v. incubating said at least one second binding agent, comprising a reactive group with a nucleic acid having a reactive group and further comprising a polymerase promoter sequence thereby forming a second binding agent-nucleic acid complex;

d. contacting the matrix-binding agent-target molecule complex formed in step (b) with the second binding agent-nucleic acid complex formed in step (c), under conditions allowing the binding of the second binding agent to the target molecule;

e. adding a DNA or RNA polymerase enzyme and nucleotides associated with a member of an affinity couple under suitable conditions to affect DNA or RNA polymerization, thereby obtaining DNA or RNA molecules associated with a member of an affinity couple, and f. contacting said DNA or RNA molecules associated with a member of an affinity couple with a complementary member of said member of an affinity couple associated with a detectable moiety;

wherein the amount of said detectable moiety is indicative of the presence of said target molecule in the sample.

In another aspect, the present invention provides a method for the diagnosis of a pathological condition in a subject comprising using a detection method in accordance with the invention as described above, wherein said target molecule is a target molecule associated with the pathological condition and wherein the amount of said detectable moiety is indicative of the presence of a pathological condition in the subject.

In another aspect, the present invention provides a method for monitoring the efficiency of a therapeutic regimen in a subject suffering from a pathological condition comprising using a detection method in accordance with the invention as described above, wherein said target molecule is an antigen associated with the pathological condition and wherein the amount of said detectable moiety is indicative of the level of the pathological condition and thereby of the efficiency of the therapeutic regimen in the subject.

In another aspect, the present invention provides kits for affecting the detection methods of the invention.

Accordingly, in one embodiment the present invention provides a kit comprising:

(a) at least one aptamer; and (b) a polymer wherein the polymer is associated with a member of affinity couple and wherein said polymer is further associated with a reactive group.

In another embodiment the present invention provides a kit comprising:

(a) at least one aptamer; and (b) a nucleic acid molecule comprising a reactive group and further comprising a polymerase promoter sequence.

In yet another embodiment the present invention provides a kit comprising:

(a) a first binding agent; and (b) a second binding agent-polymer complex, wherein the polymer is associated with a member of an affinity couple and wherein said polymer is further associated with a reactive group.

In yet another embodiment the present invention provides a kit comprising:

(a) a first binding agent; and
(b) a second binding agent-nucleic acid complex, wherein the nucleic acid in said complex comprises a reactive group and further comprises a polymerase promoter sequence.

BRIEF DESCRIPTION OF THE DRAWINGS

In order to understand the invention and to see how it may be carried out in practice, embodiments will now be described, by way of non-limiting example only, with reference to the accompanying drawings, in which.

DETAILED DESCRIPTION OF EMBODIMENTS

Figure 1A:
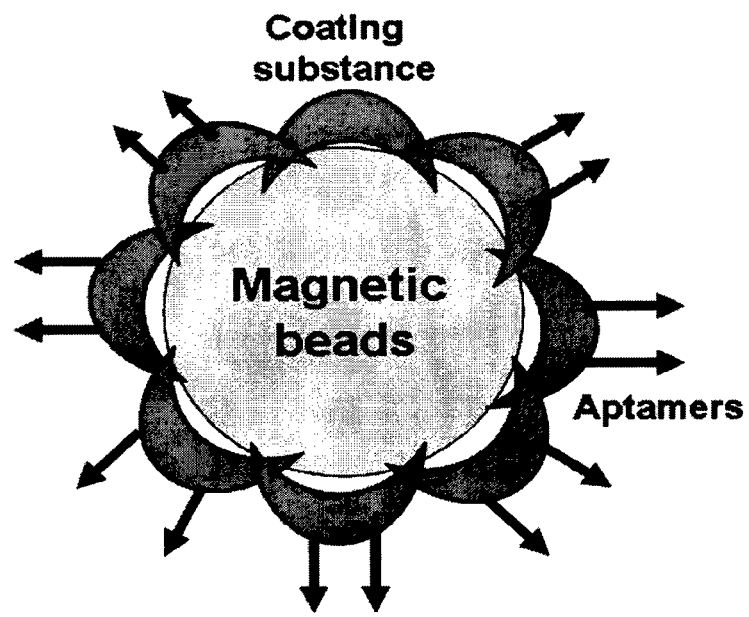
FIGS. 1A and 1B show schematic representations of modified matrix (1A) aptamers (denoted by arrows) immobilized on pre-coated magnetic beads (1B) aptamers (denoted by arrows) immobilized on pre-coated magnetic beads, which are additionally coated with cross-linkers (denoted as black dots).

The present invention provides a novel method for the detection of low levels of target molecules in a sample using a universal detection probe which enables amplification of the detection signal.

The method of the present invention is highly sensitive and can be used to detect as low as $10^3$ antigen copies or target molecules in a tested sample.

In addition, the method of the invention is accurate and provides results within a short time frame. It also involves low cost tests which in general do not involve the use of sophisticated equipment.

The following first two aspects of the invention are generally referred to herein as a "single binding agent assay" specifically "single aptamer assay". The "single binding agent assay" relates to the use of the universal detection probe in conjunction with a nucleic acid aptamer.

Thus, in accordance with the first aspect, the present invention provides a method for the detection of a target molecule in a sample comprising:

a. obtaining at least one aptamer capable of binding to said target molecule, wherein said at least one aptamer is bound to a matrix;

b. incubating said at least one aptamer which is bound to the matrix with the sample under conditions allowing the binding of the aptamer to the target molecule; thereby forming a matrix-aptamer-target molecule complex;

c. contacting the matrix-aptamer-target molecule complex formed in step (b) with a polymer associated with a member of an affinity couple wherein said polymer further comprising a reactive group; thereby forming a matrix-aptamer-target molecule-polymer complex; and d. contacting said matrix-aptamer-target molecule-polymer complex with a complementary member of said member of an affinity couple, wherein said complementary member is associated with a detectable moiety,
wherein the amount of said detectable moiety is indicative, of the presence of said target molecule in the sample.

In accordance with the second aspect, the present invention provides a method for the detection of a target molecule in a sample comprising:
  a. obtaining at least one aptamer capable of binding to said target molecule, wherein said at least one aptamer is bound to a matrix;
  b. incubating said at least one aptamer which is bound to the matrix with the sample under conditions allowing the binding of the aptamer to the target molecule; thereby forming a matrix-aptamer-target molecule complex;
  c. contacting the matrix-aptamer-target molecule complex formed in step (b) with a nucleic acid molecule comprising a reactive group and further comprising a polymerase promoter sequence, thereby forming a matrix-aptamer-target molecule-nucleic acid molecule complex;
  d. adding a DNA or RNA polymerase enzyme and nucleotides associated with a member of an affinity couple under suitable conditions to affect DNA or RNA polymerization, thereby obtaining DNA or RNA molecules associated with a member of an affinity couple, and
  e. contacting said DNA or RNA molecules associated with a member of an affinity couple with a complementary member of said member of an affinity couple associated with a detectable moiety;
wherein the amount of said detectable moiety is indicative of the presence of said target molecule in the sample.

The following two aspects of the invention are generally referred herein as "two binding agents assay". The "two binding agents assay" relates to the use of the universal detection probe in conjunction with at least two binding agents.

In accordance with the third aspect, the present invention provides a method for the detection of a target molecule in a sample comprising:
  a. obtaining at least one first binding agent capable of binding to said target molecule, wherein said first binding agent is bound to a matrix;
  b. incubating said at least one first binding agent which is bound to the matrix with the sample under conditions allowing the binding of the binding agent to the target molecule; thereby forming a matrix-binding agent-target molecule complex;
  c. contacting the matrix-binding agent-target molecule complex formed in step (b) with a second binding agent-polymer complex, wherein said second binding agent-polymer complex is obtained by either
    i. obtaining at least one biotinylated second binding agent;
    ii. incubating said at least one biotinylated second binding agent with streptavidin thereby a biotinylated second binding agent streptavidin (b-binding agent-SA) complex is formed; and
    iii. incubating said b-binding agent-SA complex formed in step (ii) with a polymer associated with a member of an affinity couple wherein said polymer further having a reactive group thereby forming a second binding agent-polymer complex; or
    iv. obtaining at least one second binding agent, wherein said at least one second binding agent comprises a reactive group; and
    v. incubating said at least one second binding agent comprising a reactive group with a polymer associated with a member of an affinity couple wherein said polymer further having a reactive group thereby forming a second binding agent-polymer complex;
  d. contacting the matrix-binding agent-target molecule complex formed in step (b) with the second binding agent-polymer complex formed in step (c), under conditions allowing the binding of the second binding agent to the target molecule, thereby obtaining a target molecule-polymer complex;
  e. contacting said target molecule-polymer complex formed in step (d) with a complementary member of said member of an affinity couple associated with a detectable moiety,
wherein the amount of said detectable moiety is indicative of the presence of said target molecule in the sample.

In accordance with the fourth aspect, the present invention provides a method for the detection of a target molecule in a sample comprising:
  a. obtaining at least one first binding agent capable of binding to said target molecule, wherein said first binding agent is bound to a matrix;
  b. incubating said at least one first binding agent which is bound to the matrix with the sample under conditions allowing the binding of the binding agent to the target molecule; thereby forming a matrix-binding agent-target molecule complex;
  c. contacting the matrix-binding agent-target molecule complex formed in step (b) with a second binding agent-nucleic acid complex, wherein said second binding agent-nucleic acid complex is obtained by either
    i. obtaining at least one biotinylated second binding agent;
    ii. incubating said at least one biotinylated second binding agent with streptavidin thereby a biotinylated second binding agent streptavidin (b-binding agent-SA) complex is formed; and
    iii. incubating said b-binding agent-SA complex formed in step (ii) with a nucleic acid having an active group and further comprising a polymerase promoter sequence thereby forming second binding agent-nucleic acid complex; or
    iv. obtaining at least one second binding agent, wherein said at least one second binding agent comprises a reactive group; and
    v. incubating said at least one second binding agent, comprising a reactive group with a nucleic acid having a reactive group and further comprising a polymerase promoter sequence thereby forming a second binding agent-nucleic acid complex;
  d. contacting the matrix-binding agent-target molecule complex formed in step (b) with the second binding agent-nucleic acid complex formed in step (c), under conditions allowing the binding of the second binding agent to the target molecule;
  e. adding a DNA or RNA polymerase enzyme and nucleotides associated with a member of an affinity couple under suitable conditions to affect DNA or RNA polymerization, thereby obtaining DNA or RNA molecules associated with a member of an affinity couple, and
  f. contacting said DNA or RNA molecules associated with a member of an affinity couple with a complementary member of said member of an affinity couple associated with a detectable moiety;
wherein the amount of said detectable moiety is indicative of the presence of said target molecule in the sample.

The "sample" according to the present invention may be any sample including, but not limited to, biological samples obtained from subjects (including humans and animals as detailed below), samples obtained from the environment for example soil samples, water samples, agriculture samples (including plant and crop samples), or food samples.

In one embodiment, said sample is a liquid sample.

The term "subject" in accordance with the invention includes but is not limited to a human, an animal, in particular, a primate, a household animal or an animal used in agriculture.

Furthermore, the term subject encompasses healthy subjects, subjects suffering from various diseases, subjects receiving various treatments, as well as deceased subjects (e.g. for forensic analysis).

In some embodiments, the biological sample may be a bodily fluid, a tissue, a tissue biopsy, a skin swab, an isolated cell population or a preparation.

In certain embodiments the cell in the population of cells or cell preparation is selected from an animal cell, a viral cell, a bacterial cell and a fungal cell.

In some specific embodiments, the population of cells comprises cancer cells. In another embodiment the population of cells is an in vitro cultured cell population.

In some embodiments, the biological sample may be a bodily fluid selected from the group consisting of blood, serum, plasma, urine, cerebrospinal fluid, amniotic fluid, tear fluid, nasal wash, mucus, saliva, sputum, broncheoalveolar fluid, throat wash, vaginal fluid and semen.

Samples according to the invention may be samples obtained from the environment for example soil samples or water samples. Water sample may be obtained for example but not limited to from drinking water, sewage, sea water, lakes, and rivers. The method disclosed in the present invention may be applied for home use, municipal use, or governmental use.

Agriculture samples may also be used, for example plant samples and crop samples. Plant samples refer to any plant or pare thereof being for example seeds, fruit, or leaves and include but are not limited to field crops or greenhouse-grown plants. The invention also encompasses plant samples obtained from wild plants (i.e. plants which are not grown by men).

Food samples may be obtained for example from fresh food, cooled food or frozen food.

The term "target molecule" as used herein denotes a molecule which may be found in a tested sample and which is capable of binding to a binding agent.

The term "binding agent" as used herein refers to any molecule capable of specifically binding to the target molecule for example an aptamer, an antibody, a receptor ligand or a molecular imprinted polymer.

In one embodiment, the target molecule is an antigen.

As used herein the term "antigen" refers to a target molecule capable of binding to a binding agent. In accordance with some embodiments, the antigen is a soluble antigen (also termed herein a "circulating antigen"), a cell-surface antigen, or an antigen associated with a micelle, a liposome or a particle.

In some embodiments, the antigen may be a protein, a polypeptide, a peptide, a ganglioside, a lipid, a phospholipid, a carbohydrate, a small molecule or a nucleic acid.

Non limiting examples of a soluble antigen in accordance with the invention are soluble cancer markers, inflammation-associated markers, hormones, cytokines, drugs, and soluble molecules derived from a virus, a bacteria or a fungus for example, toxins or allergens.

In some embodiments, the antigen is a viral antigen. In the context of the invention the term "viral antigen" is to be understood as a protein or fragment thereof encoded by the viral genome.

In some other embodiments, the antigen is a cancer (or tumor) marker. In general, a tumor marker may be found in the body fluids such as in blood or urine, or in body tissues. Tumor markers may be expressed or over expressed in cancer and are generally indicative of a particular disease process.

Non limiting examples of a cell surface antigen in accordance with the invention are a receptor, a cell surface marker, a viral antigen, or a receptor ligand.

The method of the invention may have therapeutic uses for example it may be used for the detection of various pathological conditions or may be used for monitoring the disease stage of a subject or its response to therapy.

Thus, in accordance with the fifth aspect, the present invention provides a method for the diagnosis of a pathological condition in a subject comprising using the detection methods of the invention as disclosed above, wherein said target molecule is a target molecule associated with the pathological condition and wherein the amount of said detectable moiety is indicative of the presence of a pathological condition in the subject.

In addition, in accordance with the sixth aspect, the present invention provides a method for monitoring the efficiency of a therapeutic regimen in a subject suffering from a pathological condition comprising using the detection methods of the invention as disclosed above, wherein said target molecule is an antigen associated with the pathological condition and wherein the amount of said detectable moiety is indicative of the level of the pathological condition and thereby of the efficiency of the therapeutic regimen in the subject.

The "pathological condition" according to the present invention may be selected from but not limited to cancer, inflammation, blood coagulation disorders, and autoimmunity. Accordingly, the method of the invention may be used in the detection of known cancer markers, markers of inflammation, such as Procalcitonin which is a known marker for sepsis, peptides such as penicillin-binding protein 2 (PBP2), kinesin pindle protein (KSP), toxins and alergens.

The method of the invention may be employed in the detection of a viral infection. Non limiting examples of viral infections are Hepatitis B virus (HBV), hepatitis C virus (HCV), Cytomegalovirus (CMV) (for example for the detection of CMV in transplanted patients and pregnant women), Human immunodeficiency virus (HIV), Epstein-Barr virus (EBV), HERPES virus, Polio virus and influenza virus (both Human and Avian).

The method of the invention may also be employed in the detection of a bacterial infection. Non limiting examples of bacterial causing infections are Listeria, *Staphylococcus Aureus*, Methicillin resistance *Staphylococcus Aureus* (MRSA), *Corynebacterium Diphtheriae* (causing Diphtheria), *E. coli*, Group B *streptococcus* (GBS), Group A *streptococcus, Mycobacterium Tuberculosis* (causing Tuberculosis (TB), *Salmonella, Vibrio Cholerae, Campylobacter*, Brucellosis, *Neisseria Meningitidis* (causing meningococcus), *Streptococcus pneumonia* and *Candida*.

For example, the estimated number of MRSA tests, is about 40 million per year, of which 15 millions are gene based tests. Rapid and appropriate antimicrobial therapy, including the administration of vancomycin, is critical for effective treatment. However, conventional methods for identifying MRSA, such as disc susceptibility testing, are not always reliable since phenotypic expression of methicillin resistance is known to be heterogeneous. As nucleic acid techniques such as PCR for detecting the mecA gene (Zeeshan M, et al. *comparison of different phenotypic methods of detection of methicillin resistance in staphylococcus aureus with the molecular detection of mec-a gene.* J. Coll. Physicians. Surg. Pak. 17 (2007):666-70) are expensive and technically demanding, simple and more inexpensive techniques are required for routine use.

In some embodiments, the pathological condition is cancer. Cancer is interchangeably used with the terms malignancy, tumor and is referred to herein as a class of diseases in which a group of cells display uncontrolled growth and invasion that may destroy adjacent tissues, and sometimes leads to metastasis (spreading to other locations in the body). Cancer may be a solid cancer or a non-solid cancer and may be classified as carcinoma, sarcome, lymphoma, leukemia, germ cell tumor, or blstoma.

In some further embodiments, the pathological condition is an autoimmune disease. As appreciated in the art, autoimmune diseases arise from an overactive immune response of the body against substances and tissues normally present in the body. Non limiting examples of autoimmune disease are Multiple sclerosis, Arthritis, Autoimmune hepatitis, Crohn's disease, Diabetes mellitus, type 1, Inflammatory bowel disease, Multiple sclerosis, Psoriasis, Rheumatoid arthritis, Wegener's granulomatosis.

Using the detection methods of the present invention the level of target molecules indicative of the pathological state may be determined. Therefore, the measurement of the levels of these target molecules can serve to diagnose the pathological condition, to monitor disease progression and to monitor efficacy of a therapeutic regiment, i.e. monitor the response of the subject to treatment.

According to some aspects, the method of the invention is based on the use of binding agents. In some embodiments, the binding agents may each be independently an aptamer, an antibody, a receptor ligand or a molecular imprinted polymer.

In some embodiments, the first binding agent is an aptamer.

In some embodiments, the second binding agent is an aptamer.

In some embodiments, at least one of the binding agents is a nucleic acid aptamers.

As used herein the term "complex" denotes an entity comprising more than one molecule which is bound or is in association with at least one other molecule, for example by a chemical association. Hence the term "matrix-aptamer-target molecule complex" relates to an association between the matrix, aptamer and the target molecule. The term "matrix-aptamer-target molecule-polymer complex" relates to an association between the matrix, aptamer, target molecule and the polymer. The term "matrix-aptamer-target molecule-nucleic acid molecule complex" relates to an association between the matrix, aptamer, target molecule and the nucleic acid. The term "matrix-binding agent-target molecule complex" relates to an association between the matrix, binding agent and the target molecule. The term "second binding agent-polymer complex" relates to an association between the second binding agent and the polymer. The term "biotinylated second binding agent streptavidin (or b-binding agent-SA) complex" relates to an association between biotin, a second binding agent and streptavidin. The term "target molecule-polymer complex" relates to an association between a matrix-binding agent-target molecule complex and a second binding agent-polymer complex.

As used herein, the term "aptamers" or "specific aptamers" denotes single-stranded nucleic acid (DNA or RNA) molecules which specifically recognizes and binds to a target molecule.

The aptamers according to the invention may fold into a defined tertiary structure and can bind a specific target molecule with high specificities and affinities (William James. Aptamers. In Encyclopedia of Analytical Chemistry. R. A. Meyers (2000) 4848-4871 Ó John Wiley & Sons Ltd; Pai S S, Ellington A D, *Using RNA aptamers and the proximity ligation assay for the detection of cell surface antigens.* Methods Mol. Biol. 504 (2009): 385-398).

Aptamers are usually obtained by selection from a large random sequence library, using methods well known in the art, such as SELEX and/or Molinex (William James. Aptamers. In Encyclopedia of Analytical Chemistry. R. A. Meyers (2000) 4848-4871 John Wiley & Sons Ltd; Tombelli S, et al. *Aptamers-based assays for diagnostics, environmental and food analysis.* Biomol Eng. 24 (2007):191-200).

According to the present invention and as appreciated in the art, the recognition between the aptamer and the antigen is specific and may be detected by the appearance of a detectable signal by using a colorimetric sensor or a fluorimetric/lumination sensor.

The aptamers as used according to some aspects of the invention may be biotinylated.

The aptamers may optionally include a chemically reactive group at the 3' and/or 5' termini. The term reactive group is used herein to denote any functional group comprising a group of atoms which is found in a molecule and is involved in chemical reactions.

Some non-limiting examples for a reactive group include primary amines ($NH_2$), thiol (SH), carboxy group (COOH), phosphates (PO4), Tosyl, and a photo-reactive group.

In some embodiments, the aptamer as used herein may optionally comprise a spacer between the nucleic acid sequence and the reactive group. The spacer may be an alkyl chain such as $(CH_2)_{6/12}$, namely comprising six to twelve carbon atoms.

According to the present invention, the aptamers are bound to a matrix. The matrix according to the invention may be for example any support structure or a surface. Non limiting examples include beads, e.g. magnetic beads, agarose beads, sephadex beads, glass beads, flat surfaces such as a culture plate, a well in a plate, a tube surface, quantum dots, resins, plastic paper, nitrocellulose membranes, particle, microsphere and Molecular imprinted Polymers (MIP) (Michael J. et al. *The rational development of molecularly imprinted polymer-based sensors for protein detection*, Chem. Soc. Rev., 40 (2011): 1547-1571).

The magnetic beads may be selected from but not limited to Tosylactivated beads or Streptavidin coated "MyOne" and "M280" Dyna-Beads (BD, Invitrogen).

Figure 1B:
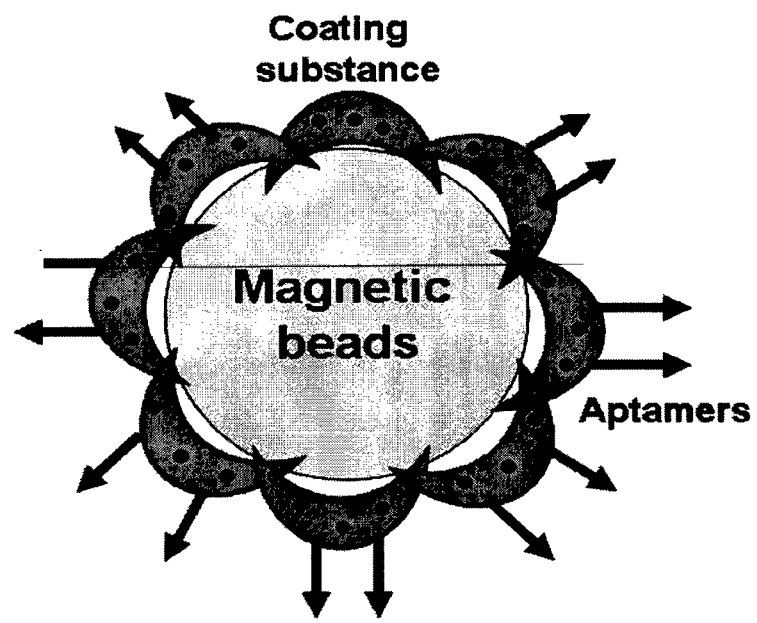

While working with magnetic beads, all related procedures are performed as directed by the manufacturer. All washings are performed by employing a Magnetic separator. FIG. 1 provides an example of magnetic beads suitable for use in the present invention.

The matrix is initially pre-blocked in order to reduce or eliminate non specific binding by any suitable blocking agent known in the art. Non limiting examples of coating materials are protein, acryl amide, synthetic polymer and polysaccharides.

In some embodiments, coating may be for example by covalently binding of blocking proteins such as bovine serum albumin (BSA), streptavidin, avidin, extravidin or any modification thereof.

In some further embodiments, coating may be by any low affinity binding protein or polymer.

In certain embodiments the matrix may be activated for example by pre-coating with a compound selected from a group consisting of polylysine, epoxy, tosyl, carboxylic acid, carboxylated polyvinyl alcohol and photoreactive crosslinkers. Examples of photoreactive crosslinkers include but are not limited to simple aryl azides, fluorinated aryl azides or benzophenone derivatives.

In some embodiments, an activated matrix includes molecularly imprinted polymers (MIP), antibody associated, or ligand associated matrix.

As used herein the term "activated matrix" refers to a matrix which can be covalently bound to a first binding agent, for example an aptamer or a suitably modified aptamer. Said activated matrix is obtained by coating the matrix with a suitable material, for example as listed above.

The first binding agent, for example the aptamers may be attached to the pre coated matrix, for example by covalently binding to the coating protein.

For example, in an embodiment whereby a streptavidin coated matrix is used, the first binding agent is biotinylated. For example biotinylated aptamers may be preferably used.

According to this embodiment, the aptamers according to the different aspects of the invention are biotinylated and the matrix is pre-coated with streptavidin, the aptamer is bound to the matrix via streptavidin biotin binding, thereby forming an aptamer-matrix complex.

In an embodiment whereby a protein-coated matrix is used (for example, a BSA-coated matrix), primary $NH_2$ or SH labeled aptamers may be preferably used by employing homobifunctional crosslinkers or heterobifunctional cross linkers.

As used herein the term "crosslinkers" refers to cross-linking reagents which contain two or more reactive ends capable of chemically attaching to specific functional groups (primary amines, sulfhydryls, etc.) on proteins or other molecules.

According to some embodiments, the first binding agent of the present invention for example the aptamer, comprises reactive groups and the matrix is pre-coated with a protein, the first binding agent is bound to the matrix by adding a cross linking agent, thereby forming a first binding agent-matrix complex. In some specific embodiments, an aptamer-matrix complex is formed.

Homobifunctional crosslinkers are reagents that have the same type of reactive group at either end. Amine crosslinkers (namely bind amine reactive groups) may be selected for example from glutaraldehyde, bis (imidoesters) or bis (succinimidylesters) (also known as NHS esters).

According to some specific embodiments, homobifunctional crosslinkers such as but not limited to dimethyl pimelimidate (DMP) or Glutaraldehyde can bind to primary $NH_2$ groups on the BSA surface and to $NH_2$ groups the aptamers. Sulfhydryl crosslinkers may be selected for example from maleimides, or pyridyldithiols.

The crosslinking may be non-specific by using reactive groups such as aryl azides.

Heterobifunctional crosslinkers are reagents that have different type of reactive group at either end for example but not limited to amine-to-sulfhydryl or amine-to-carboxyl.

Amine-to-Sulfhydryl crosslinkers may have NHS esters and maleimides at each end, or NHS esters and pyridylithiols at each end.

According to some specific embodiments, the heterobifunctional crosslinkers may bind the primary $NH_2$ groups on the BSA surface, and the aptamer via the SH tail.

Examples of heterobifunctional crosslinkers that can bind amine and Sulfhydryl groups are selected from but not limited to N-Succinimidyl 3-[2-pyridyldithio]-propionate (SPDP), Succinimidyl-4-(N-maleimidomethyl)cyclohexane-1-carboxylate (SMCC), or Succinimidyl-4-(p-maleimidophenyl) butyrate (SMPB).

Following the first binding agent binding to the matrix, further steps are preferably performed prior to the target molecule binding and detection in order to block any reactive group on the matrix surface, with which the chemically reactive groups on biotinylated polymer may interact.

In some embodiments, the blocking agent is thereby blocking the remaining free reactive groups on the matrix such as but not limited to primary $NH_2$ groups, SH groups and carboxyl groups.

For example, blocking agents such as DMP, Citraconic Anhydride (CA), Sulfo-NHS-Acetate glutaraldehyde, photo-reactive groups, N-acetylcysteine and N,N'-Methanetetraylbis (2-propanamine) (DIPCDI) may be added. These agents will bind and block for example primary $NH_2$ groups, preferably without affecting the protein charge or hydrophilic and/or hydrophobic state.

In some embodiments, DMP or CA may be used as blocking agents.

According to this embodiment, free DMP having unbound moieties is blocked by the addition of primary $NH_2$ compounds such as TRIS and Urea.

As can be appreciated, following first binding agent or aptamer binding to the matrix and the chemical blocking, there are no free unbound reactive groups such as primary $NH_2$ groups or SH groups on the formed matrix-first binding agent or matrix-aptamer complex.

Hence upon incubation with the antigen containing sample (as will be described in detail below), the only unbound reactive groups being for example primary $NH_2$ groups will be those of the antigen.

Following the formation of the matrix-first binding agent or matrix-aptamer complex a universal detection probe is added as detailed below.

According to some embodiments, the present invention provides methods for detecting the presence of a target molecule by using at least one aptamer.

As detailed above, a single type of aptamer may be used (referred herein as "single binding agent assay" or "single aptamer assay"), preferably used in the detection of soluble antigens such as proteins.

In some embodiments, at least two of binding agents ("two binding agents assay") may be used in a sequential manner for the detection of target molecules. According to some embodiments, the at least two binding agents, referred to herein as first binding agent and second binding agent, are of the same class of agents for example being two aptamers (referred to herein as the "dual aptamer assay"). In some further embodiments, the first binding agent and the second binding agent are of a different class of agents.

According to some specific embodiments, the first binding agent is an aptamer and the second binding agent is an antibody. In some further specific embodiments, the first binding agent is an aptamer, antibody or MIP and the second binding agent is an aptamer.

In some embodiments, the first binding agent and the second binding agent are directed towards the same target molecule or towards different target molecules. In some embodiments, the first binding agent and the second binding agent are targeted to different epitopes on the target molecule.

In some specific embodiments, two different aptamers are used ("dual aptamer assay" or "two aptamer assay").

In some specific embodiments, multiple different aptamers are used.

According to some embodiments, the two binding agents assay is preferably used for the detection of cell associated antigens.

According to these embodiments, the first binding agent may be used to identify a population of cells, and a second, different binding agent may be used to detect a specific target antigen, e.g. a surface protein.

In one embodiment, the second binding agent may for example detect a subpopulation of cells, within the cells which are detected by the first binding agent.

Non limiting examples for the use of the two binding agents assay may be for example for the detection of cell surface associated cancer markers or detection of viral markers on host cell surface. In a specific embodiment, the two compartment assay may be used in a CMV antigenemia test for the identification of CMV infection in organ/bone marrow transplant patients (Raymond U. et al. *CMV Antigenemia Following Bone Marrow Transplantation: Risk Factors and Outcomes*. The 2000 American Society for Blood and Marrow Transplantation, 17 (2000): 280-288).

In some embodiments, the sample is incubated with the first binding agent-coated matrix obtained as described above. The incubation enables the target molecule to bind to the first binding agent-matrix complex.

According to the "single aptamer assay" embodiment the target molecule attached to the at least one aptamer bound to the matrix is further incubated in the presence of a water soluble polymer which carries a chemical reactive group.

According to some other embodiments of the invention, more than one aptamer may be used in the assay.

According to the "two binding agents assay" the target molecule attached to the first binding agent bound to the matrix is further incubated in the presence of a second binding agent bound to a water soluble polymer which carries a chemical reactive group.

In the context of the present invention, the term "polymer" denotes any molecule consisting of a repeating unit capable of being associated with a member of an affinity couple. In the context of the present invention, the chemical reactive group may be for example a succinimidyl Ester (SE) group (for interacting for example with primary $NH_2$ on the aptamer).

The term "affinity couple" as used herein denotes any two groups having a high affinity of interaction namely, binding. Non-limiting examples for affinity couples are biotin/avidin, antigen/antibody, Molecular Imprinted Polymers/target ligand, protein-A/IgG, ligand/receptor, and a nucleic acid molecule/complementary sequence.

It is to be understood that the term "a member of an affinity couple" as used herein denotes one member of the affinity couples exemplified above.

The member of an affinity couple may be bound to the polymer via a reactive group. Non limiting examples of a reactive group are primary amines ($NH_2$), Sulfhydryls (SH), Carboxyls (COOH), Carbonyls (—CHO) or any other reactive group which is capable of binding a member of an affinity couple and is directed against the chosen target chemical group on the antigen surface.

According to some embodiments, the second binding agent is incubated with streptavidin (SA) thereby a biotinylated second binding agent streptavidin (b-binding agent-SA) complex is formed for example in a molar ratio of 1:5, optionally followed by the addition of free biotin (molar ratio of 1:5 to SA) to block any free biotin site on the SA. The second binding agent may be different or identical to the first binding agent.

In this embodiment, the b-binding agent-SA complex is incubated with a polymer associated with a member of an affinity couple and the polymer further having a reactive group thereby forming a second binding agent-polymer complex In some further embodiments, the second binding agent binds to the polymer associated with a member of an affinity couple.

The second-binding agent-polymer complex is then added to the matrix-first binding agent-antigen complex.

Figure 3:
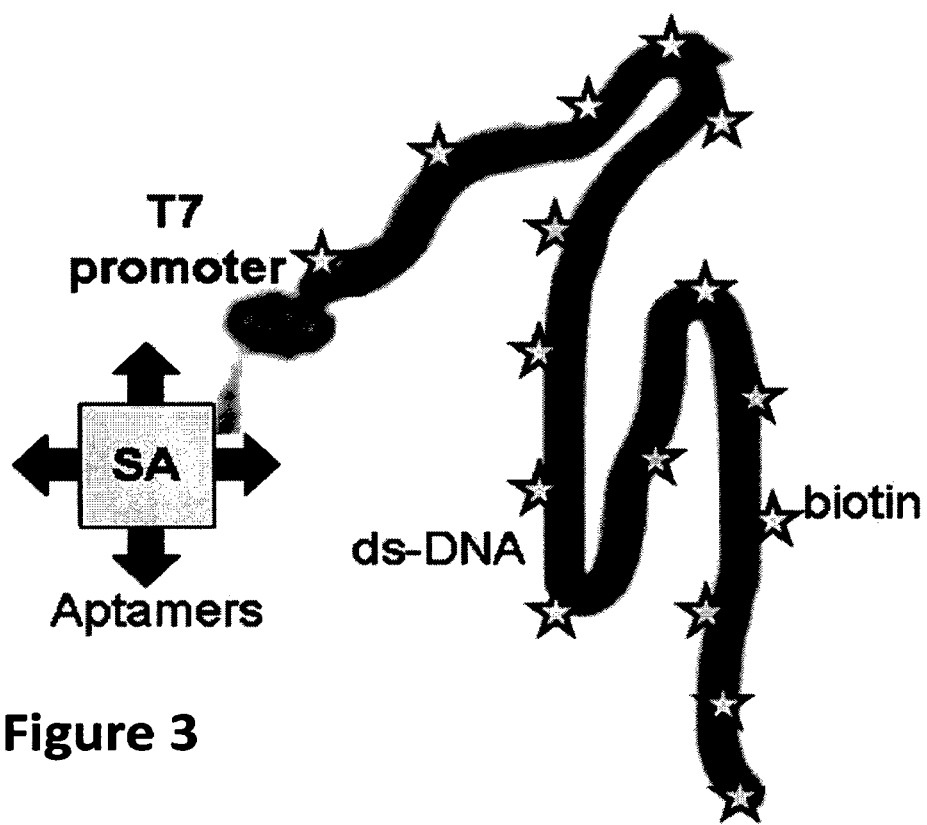
FIG. 3 shows a schematic representation of the complex used in the "dual aptamer assay", which is formed by the streptavidin (SA)-aptamer complex and the b-ds-DNA-SE.

In some specific embodiments, b-ds-DNA-SE is added to the complex of SA-second binding agent being an aptamer for example at a molar ratio of 2-5:1 (DNA:SA) as schematically shown in FIG. 3. The aptamers/SA/b-ds-DNA-SE complex may be further purified on an exchange column, e.g. a sephadex G25 column.

In some embodiments, the water soluble polymer comprises $CH_2$ groups, organic groups or nucleic acids.

Figure 2A:
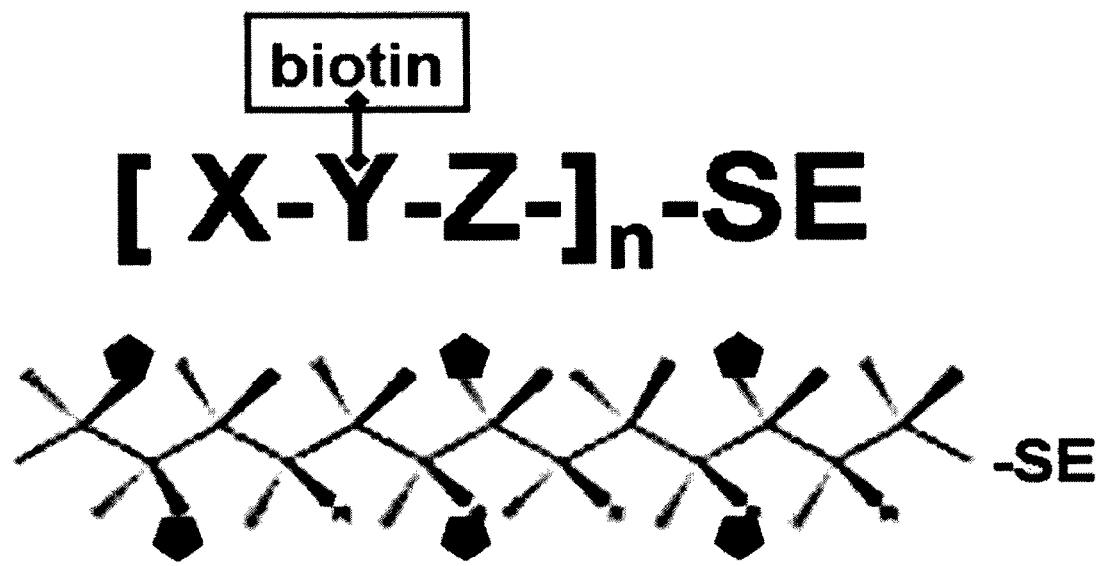
FIGS. 2A and 2B are schematic representations of a biotinylated polymer, which is incubated with the antigen-aptamer-matrix complex (2A) A general formula of the biotinylated polymer, which consists of n repeating units, carries a reactive group and binds to a succinimidyl ester (SE) group (2B) A specific example of the polymer being a biotinylated double strand-DNA carrying a succinimidyl group ("b-ds-DNA-SE").

In some specific embodiment the member of an affinity couple is biotin (FIG. 2A).

In some other embodiments, the polymer is a DNA. In some specific embodiments, the polymer is a single stranded (ss-DNA) or double-stranded DNA (ds-DNA).

In some aspects wherein the polymer is a DNA, it may be obtained from any source (e.g. human, animal, bacterial, viral, fungal, plant or synthetic sources). Preferably, a synthetic DNA sequence is used, in order to avoid similarity and potential cross reactivity to plant, animal, human, bacteria or viral antigens.

The ds-DNA is inserted into a vector, e.g. a plasmid, for example a pGEM-T, (Promega USA) according to Manufacturer's instructions and using methods well known in the art.

The constructed plasmid may be subsequently subjected to PCR (polymerase chain reaction) by using for example a forward, T7, 5'-$NH_2$ or SH or biotin labeled primer and a reveres, SP6 primer. The 3'/5' direction of the SP6/T7 primers can be replaced.

The invention is not limited to a particular size of the ds-DNA. In particular embodiments, the size of the ds-DNA molecule may be for example between about 1 kb to about 5 kb, namely the molecule may be of any size within that range, e.g. about 3 kb.

In the context of the present invention the term "about" is used to denote an approximated range of more or less 10% of the indicated value.

According to some specific embodiments, the synthesis of the ds-DNA is preformed in the presence of nucleotides associated with a member of an affinity couple, using a 5'/3'-modifided primer, thereby obtaining a ds-DNA molecule associated with a member of an affinity couple.

In a specific embodiment, biotinylated dNTP (nucleoside triphosphates) nucleotides may be added during the PCR process, to create biotinylated ds-DNA. In a specific embodiment, by using the ratio for biotin/non-biotin NTP of 1:5, about 250 biotin groups may be associated with a ds-DNA molecule of about 3.5 kb.

The present invention provides methods for an alternative or an added signal amplification step. This signal amplification step may be used in both the "single aptamer assay" and in the "two binding agents assay".

In some further embodiments, the ds-DNA molecule further comprises at least one RNA polymerase promoter sequence. For example, the T7 and/or SP6, M13 RNA polymerase promoter sequence.

According to this embodiment, nucleotides associated with a member of an affinity couple are added to affect DNA or RNA polymerization, thereby obtaining DNA or RNA molecules associated with a member of an affinity couple.

In some embodiments, the DNA molecule comprises a reactive group at its 5' and/or 3' termini. In some embodiments, the reactive group is succinimidyl ester (SE).

According to these embodiments, SE may be subsequently attached to the ds-DNA associated SH group by reacting the biotin ds-DNA with a compound that can react with the SH group. For example compounds from the maleimids family may be used such as but not limited to Succinimidyl-4-(p-maleimidophenyl) butyrate (SMPB), Sulfo-Succinimidyl-4-(p-maleimidophenyl) butyrate (s-SMPB), Succinimidyl-4-(N-maleimidomethyl)cyclohexane-1-carboxylate (SMCC), Sulfosuccinimidyl-4-(N-maleimidomethyl)cyclohexane-1-carboxylate (Sulfo-SMCC).

Figure 2B:
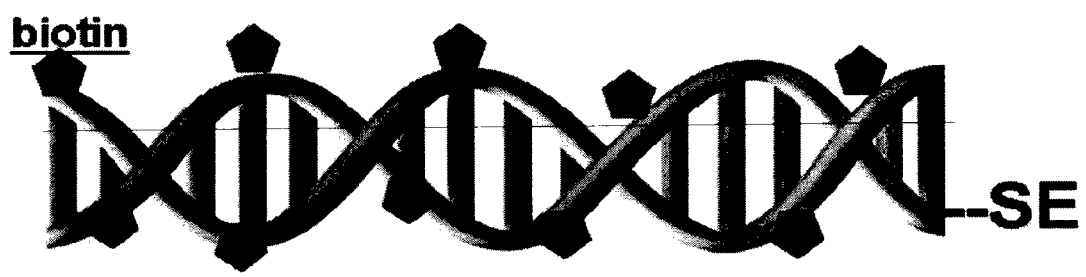

The synthesized product obtained thereby is a dsDNA carrying a succinimidyl group (biotin-ds-DNA-SE), which may covalently bind to primary $NH_2$ groups on the antigen. A schematic representation of the molecule is shown in FIG. 2B.

According to some specific embodiments, the biotin-ds-DNA-SE may directly bind the antigen, which is already bound to the aptamer (through specific aptamer-antigen recognition).

According to a specific embodiment, binding of biotin-ds-DNA-SE to the antigen may be for example by covalently binding the antigen's primary $NH_2$ group, preferably from Lysine and/or Arginine residues.

As detailed above, it is appreciated, that all other primary $NH_2$ groups from the proteins coating the matrix have been pre-blocked (e.g. by the addition of DMP or CA). The present invention encompasses the use of detectable signal amplification methods well known in the art.

In some embodiments, the polymer associated with a member of an affinity couple and signal detection is obtained by adding a complementary member of said member of an affinity couple associated with a detectable moiety.

It is to be understood that the term "a complementary member" as used herein denotes the complementary member within each couples.

Affinity couple as used herein denotes any two groups having a high affinity of interaction namely, binding. Non-limiting examples for affinity couple is selected from the group consisting of biotin/avidin, antigen/antibody, Molecular Imprinted Polymers/target ligand protein-A/IgG, ligand/receptor, and a nucleic acid molecule/complementary sequence.

The term "detectable moiety" as used herein denotes any compound capable of producing a detectable signal. According to the present invention, the detectable moiety is selected from a chromophore, a fluorophore or a luminancephore.

Specific examples include but are not limited to enzyme-labeled fluorescence (ELF), Hybridization signal amplification method (HSAM), radioactivity-based hybridization assays.

In some embodiments, the member of an affinity couple is biotin and the complementary member of said member is any anti-biotin molecule such as for example avidin or modifications or derivatives thereof (e.g. streptavidin).

Figure 4A:
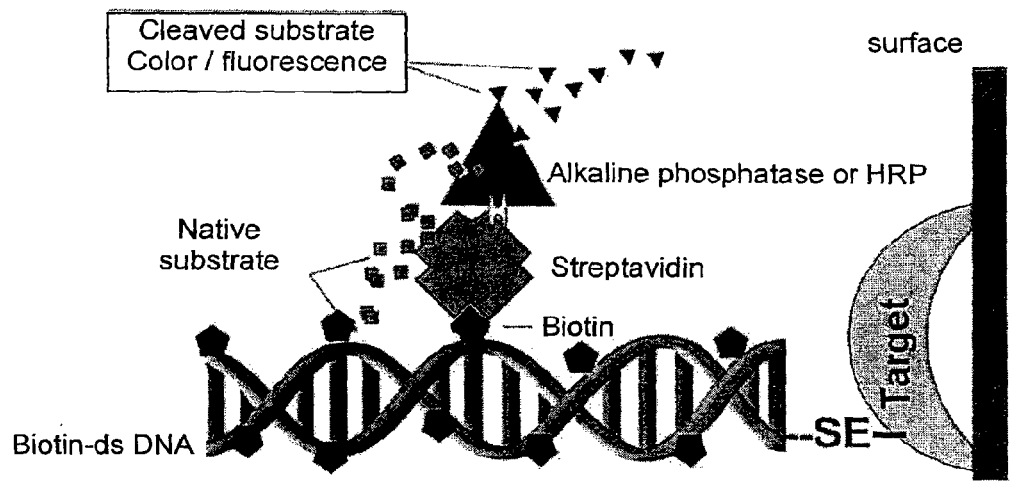
FIGS. 4A and 4B show schematic representation of the amplification methods according to the invention (4A) enzyme-labeled amplification obtained by the addition of streptavidin covalently coupled to either horseradish peroxidase (HRP) enzyme or alkaline phosphatase (AP), which binds to the biotinilayed polymer, followed by the addition of the related substrate. (4B) Additional amplification obtained by converting the ds-DNA, by using the T7 or SP6 promoter sequences located on the ds-DNA and the addition of biotinylated NTP in the T7/SP6 RNA polymerase reaction, into biotinylated RNA, which may then be transferred to an avidin labeled matrix for detection.

In some embodiments, signal amplification may be achieved by enzyme-labeled fluorescence by adding for example avidin or streptavidin covalently bound to horse-radish peroxidase (HRP) enzyme or alkaline phosphatase (AP) enzyme, (HRP/AP=SA), followed by the addition of the related substrate and monitoring the signal with the related photometer as demonstrated in FIG. 4A. As appreciated, Alkaline Phosphatase (AP) or Horse Radish Peroxidase (HRP) substrate detection may be achieved by chromatic signal, fluorescence signal or luminescence signal, which may be detected using various spectrophotometers and fluorometers.

Enzyme-Labeled Fluorescence (ELF) (Paragas V B, Zhang Y Z, Haugland R P, Singer V L. *The ELF-97 alkaline phosphatase substrate provides a bright, photostable, fluorescent signal amplification method for FISH*. J. Histochem. Cytochem. 45 (1997):345-57) and Hybridization signal amplification method (HSAM) (Kerstens H M, Poddighe P J, Hanselaar A G. *A novel in situ hybridization signal amplification method based on the deposition of biotinylated tyramine*. J. Histochem. Cytochem. 43 (1995):347-52), were developed as an alternative, non-radiation hybridization based system for the sensitive and rapid identification of DNA and RNA and semi-quantification in histochemical assays such as: in situ hybridization techniques and Northern and Southern blot analyses (Kerstens H M, Poddighe P J, Hanselaar A G. *A novel in situ hybridization signal amplification method based on the deposition of biotinylated tyramine*. J. Histochem. Cytochem. 43 (1995): 347-52; Peter Birner, Barbara Bachtiary, et al. *Signal-Amplified Colorimetric In Situ Hybridization for Assessment of Human Papillomavirus Infection in Cervical Lesions*. Mod. Pathol. 14 (2001):702-709). The test uses a method that creates a chromic, fluorescence or luminescent signal whose brightness depends on the amount of nucleic acid present. Test results are calibrated in numbers of nucleic acid particle equivalents per tested phase. The ELF test is similar in results but not in technique to the PCR test (Peter Birner, Barbara Bachtiary, et al. *Signal-Amplified Colorimetric In Situ Hybridization for Assessment of Human Papillomavirus Infection in Cervical Lesions*. Mod. Pathol. 14 (2001):702-709).

In general, the enzyme catalyzes a reaction of a substrate which generates light signal (detectable in spectrophotometer, fluorometer or luminometer). The amount of light emitted increases with the amount of the specific nucleic acid present in the sample (Paragas V B, Zhang Y Z, Haugland R P, Singer V L. *The ELF-97 alkaline phosphatase substrate provides a bright, photostable, fluorescent signal amplification method for FISH*. J. Histochem. Cytochem. 45 (1997): 345-57).

According to some embodiments, the nucleic acid molecule comprises a reactive group and further comprises a polymerase promoter sequence. According to these embodiments, the nucleic acid molecule is not associated with a member of the affinity couple prior to binding to the antigen (in the "single aptamer assay") or to the second binding agent (in the "two binding agents assay"). According to some embodiments, in the "single aptamer assay" the nucleic acid molecule comprising a reactive group and further comprising a polymerase promoter sequence binds to the antigen, for example by binding the antigen's primary $NH_2$ groups, preferably from Lysine and/or Arginine residues.

As detailed above, it is appreciated, that all other primary $NH_2$ groups from the proteins coating the matrix are blocked by the addition of, for example DMP.

According to other embodiments, in the "two binding agents assay", nucleic acid molecule comprising a reactive group and further comprising a polymerase promoter sequence binds to the second binding agent as detailed above.

In some embodiments, signal amplification may be achieved by converting the nucleic acid being ds-DNA into RNA, by using the T7 or SP6 promoter sequences located on the nucleic acid and the addition of nucleotides associated with a member of an affinity couple in the T7/SP6 RNA polymerase reaction.

In some embodiments, the RNA or DNA molecules associated with a member of an affinity couple are contacted with a complementary member of said member of an affinity couple associated with a detectable moiety.

For example RNA or DNA molecules are anchored to a matrix coated with a complementary member of said member of an affinity couple.

Figure 4B:
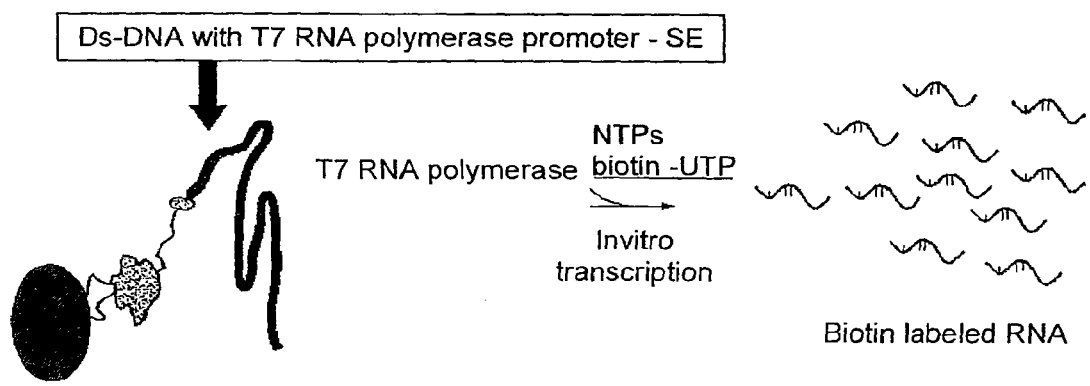

In some embodiments, the RNA molecule associated with a member of an affinity couple may then be transferred to a matrix labeled with a complementary member of said member of an affinity couple for detection as schematically shown in FIG. 4B.

In some specific embodiments, the DNA comprising a polymerase promoter sequence is incubated in the presence of biotinylated NTPs under suitable conditions to affect DNA or RNA polymerization.

In some embodiments, the formed biotinylated RNA is anchored to an avidin coated tube or beads with simultaneous or subsequent addition of HRP or AP.

In some specific embodiments, branched DNA assay may be performed.

As appreciated, branched-DNA is essentially a sensitive hybridization technique which involves linear amplification (Edmonds M. Branched RNA. BioEssays 212-21). The Branched-DNA Signal Amplification Assay is an alternative hybridization based system for the sensitive and rapid detection of nucleic acids (Edmonds M. Branched RNA. BioEssays 6: 212-21; Chien-Hung chen et al. *Quantitative detection of hepatitis B virus DNA in human sera by branched-DNA signal amplification*. J. of virological methods, 53 (1995):131-137). The test uses a method that creates fluorescence/luminescent signal whose brightness depends on the amount of nucleic acid present. The Branched-DNA test is similar in results but not in technique to the PCR test (Tao Chen, et al. *Valuation of Quantitative PCR and Branched-Chain DNA Assay for Detection of Hepatitis B Virus DNA in Sera from Hepatocellular Carcinoma and Liver Transplant Patients*. J. of Clinical Microbiology, 38 (2000): 1977-1980).

Several different oligonucleotides are used in a Branched-DNA assay. In the first stage, the oligonucleotides are used to capture and encore the target nucleic acid onto a solid support. Employing DNA hybridization techniques DNA branch units are being built, and HRP or AP strep-avidin complexes are being associated with the "branch" biotinylated oligonucleotides, thereby creating a dense decoration of the DNA with the enzyme, allowing high sensitivity of the assay (Edmonds M. Branched RNA. BioEssays 6: 212-21).

According to these embodiments, a PCR product is generated as described above by using a forward thiol labeled primer and a reverse biotin labeled primer.

The ds-DNA, PCR product, is separated to single strands, for example by incubating the ds-DNA with strepavidin coated magnetic beads and heating to 95° C. to enable separation of the two DNA strands. The biotinylated DNA strand is then removed by precipitating the beads.

Figure 5A:
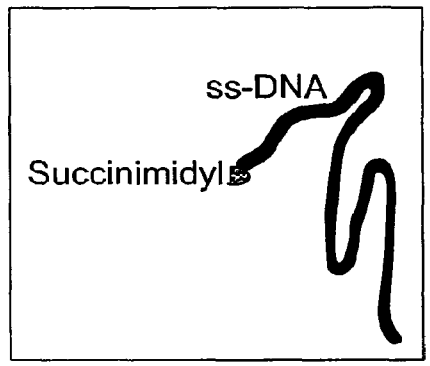
FIGS. 5A to 5D show a schematic representation of the branched DNA assay (5A) the ss-DNA-SE complex formed by incubating the thiol labeled ss-DNA with s-SMPB or s-SMCC, which reacts with thiol residual groups on the ss-DNA (5B) the aptamer-SA-ss-DNA complex formed by binding of the SE group from the ss-DNA to the primary $NH_2$ groups of the SA (5C) A pre-prepared ss-DNA sequence directed branch unit comprising AP and HRP (5D) the branch unit (according to the selected directed ss-DNA sequences) attached to the ss-DNA
Figure 5B:
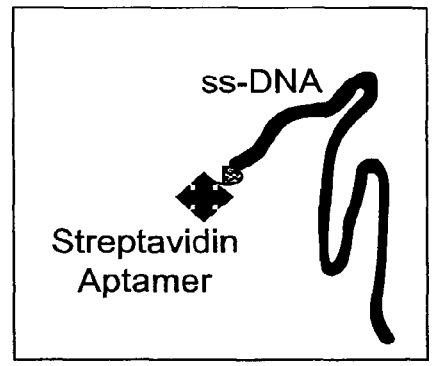

The thiol labeled ss-DNA strand is then incubated with s-SMPB or s-SMCC, which reacts with SH residual groups on the ss-DNA strand, to form a ss-DNA chain attached to a succinimidyl group—ss-DNA-SE, that can bind to a captured antigen primary $NH_2$ groups (FIG. 5A). For two aptamers assay, the succinimidyl ester group may bind to a complex of SA-aptamers by the binding of the succinimidyl group from the ss-DNA to the primary $NH_2$ groups of the SA. This results in formation of a complex of aptamer-SA-ss-DNA (as schematically shown in FIG. 5B).

It is noted that the ss-DNA is anchored to the beads as it is covalently bound to the antigen, therefore, the first stage of the DNA branch technique is eliminated, i.e. anchoring the ssDNA to the matrix by multiple primer hybridization and full DNA sequence can be used for branched associate hybridization.

Figure 5C:
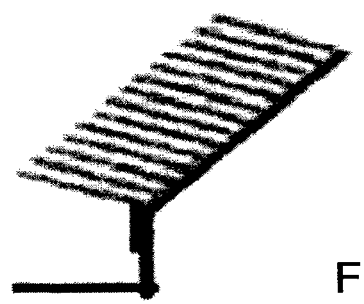
Figure 5D:
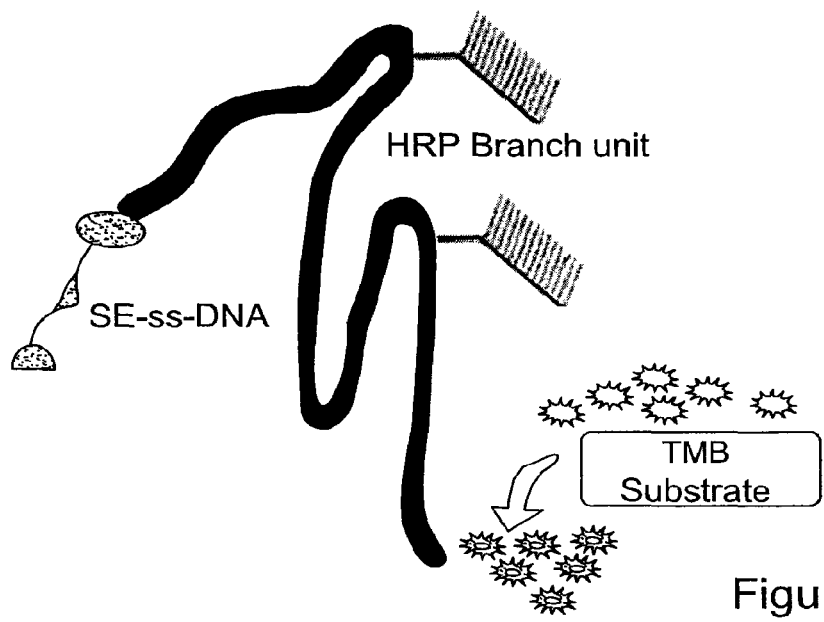

Next, using LNA (locked nucleic acid), in order to strengthen the hybridization, a Branch unit is constructed. See schematic representation in FIGS. 5C and 5D. According to one aspect of the invention, the detection methods provide a qualitative or a non-quantitative assessment of the presence of the target antigen.

When employing SA/Aptamers/b-DNA complex in certain embodiments, such as detecting cell-surface antigens (for example bacterial surface antigens), gravitation (e.g. centrifugation) may be used for cell separation and washing and thereby avoiding the use of an additional capture particle bead or surface as described above.

In general, 5' labeled Biotin, $NH_2$ and SH primers and Aptamers are commercially available. Reaction buffers are selected according to manufacturer's suggestion in each stage. Commercially available PCR compounds, Magnetic beads, cross linkers, SA, SA=AP/HRP and AP/HRP substrate are used according to the manufacturer's instructions with required modifications, as detailed. Modified Branch-DNA assay is constructed according to the selected DNA sequences.

In one specific embodiment, the present invention provides a method for the detection of a target molecule in a sample comprising:

a. obtaining at least one aptamer capable of binding to said target molecule, wherein said at least one aptamer is bound to a matrix;

b. incubating said at least one aptamer which is bound to the matrix with the sample under conditions allowing the binding of the aptamer to the target molecule; thereby forming a matrix-aptamer-target molecule complex;

c. contacting the matrix-aptamer-target molecule complex formed in step (b) with a biotinilated nucleic acid molecule wherein said biotinilated nucleic acid molecule further comprising SE; thereby forming a matrix-aptamer-target molecule-biotinilated nucleic acid complex; and d. contacting said complex obtained in step (c) with streptavidin associated with HRP or AP and a suitable substrate, wherein the amount of detectable signal produced by the substrate is indicative of the presence of said target molecule in the sample.

In accordance with a further aspect, the present invention provides a kit comprising (a) at least one aptamer; and (b) a polymer wherein the polymer is associated with a member of an affinity couple and wherein said polymer is further associated with a reactive group.

In accordance with some further aspect, the present invention provides a kit comprising
(a) at least one aptamer; and
(b) a nucleic acid molecule comprising a reactive group and further comprising a polymerase promoter sequence.

In some embodiments, the kit is provided herein is for use in a "single aptamer assay".

In accordance with yet a further aspect, the present invention provides a kit comprising
(a) a first binding agent; and
(b) a second binding agent-polymer complex, wherein the polymer is associated with a member of an affinity couple and wherein said polymer is further associated with a reactive group.

In accordance with yet a further aspect, the present invention provides a kit (a) a first binding agent; and
(b) a second binding agent-nucleic acid complex, wherein the nucleic acid in said complex comprises a reactive group and further comprises a polymerase promoter sequence.

In some embodiments, the kit provided herein is for use in a "two binding agents assay".

According to some embodiments, the polymer is a nucleic acid.

According to some embodiments, the polymer is biotinylated.

According to some embodiments, the active group is a succinimidyl ester group.

According to some embodiments, the aptamer is bound to a matrix.

According to some embodiments the first binding agent is bound to a matrix.

In some embodiments, each of the first or second binding agents independently is selected from the group consisting of an aptamer, an antibody, a receptor ligand or a MIP.

The kits according to the invention may comprise reaction buffers and/or washing buffers and/or instructions for use.

In some further embodiments, the nucleic acid is not associated with a member of the affinity couple. In some specific embodiments, the nucleic acid is a non biotinylated ds-DNA.

In some embodiments, the polymer is associated with a member of the affinity couple. In some specific embodiments, the polymer is a biotinylated ds-DNA.

In some further embodiments, the ds-DNA comprises RNA or DNA polymerase enzyme.

The kits according to the invention may further comprise RNA or DNA polymerase enzyme, NTPs, and NTPs associated with a member of an affinity couple. The member of an affinity couple is for example biotin.

The kits may also comprise at least one detection enzyme and optionally a substrate for said detection enzyme, which is HRP or AP.

Figure 6:
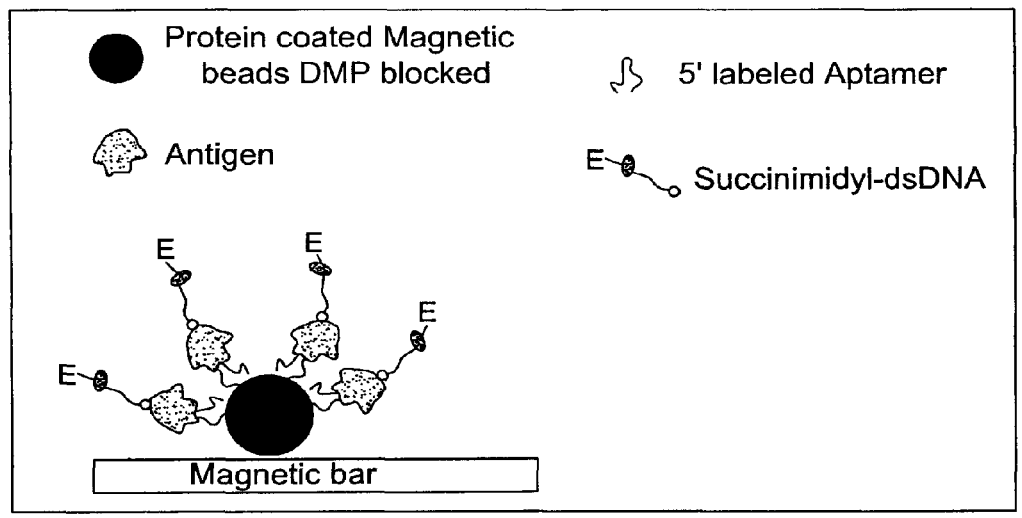
FIG. 6 shows a schematic illustration of the "single aptamer assay".

FIG. 6 shows a schematic illustration of the "single aptamer assay".

In accordance with one example of the the single aptamer assay, the aptamer is covalently bound to the matrix, for example to magnetic beads, and is further used to detect target antigen.

In a non limiting example of the present invention, the assay comprises the following steps:

In the first step, a complex comprising a matrix (which may be pre-coated as described above), for example magnetic beads, is bound to an aptamer, possibly a biotinylated aptamer and is incubated with a test sample allowing the aptamers to bind to the tested antigen. The matrix, now containing the bound antigen, is obtained from the sample.

In the second step for example a biotinylated ds-DNA-SE is added and covalently binds the antigen.

In some specific embodiments, if the ds-DNA-SE is not biotinylated, a T7/SP6 RNA polymerase amplification reaction is performed at this step, preferably in the presence of biotinylated dNTPs resulting in obtaining a biotinylated RNA molecule, as described above, followed by binding the biotinylated RNA molecule onto a SA matrix. Alternatively, ss-DNA complexes are to the antigen.

In the third step, a modified Enzyme-Labeled Fluorescence Signal Amplification step is performed, by adding SA=HRP/AP reagent, followed by the addition of the related substrate.

In one embodiment wherein ss-DNA is used, a Branched DNA complex is formed before adding the SA=HRP/AP reagent.

In some specific embodiments the first two steps or at least the second step may be skipped. In such embodiments, the aptamer-SA-bDNA complex is used.

In some embodiments, all the steps are performed in a single test tube.

In some other embodiments, the assay is performed in several test tubes. For example, steps 1 and 2 including the RNA amplification are performed in one Tube and step 3 is performed in another tube.

According to some embodiments of the invention, step 2 of the assay can be performed in two main formats: using ds-DNA or ss-DNA. In embodiments wherein ss-DNA is used, the RNA polymerase step is eliminated, and a step of "branched" DNA formation may be added. It is noted that in the case of RNA amplification, The RNA can be bound to SA-magnetic beads (or other matrix), and a branched-RNA assay can be performed.

In accordance with the "single aptamer assay" embodiment, the present invention provides means to detect and quantitate (or semi-quantitate) a soluble antigen such as a protein or any other antigen which carries a reactive group, e.g. free primary $NH_2$ groups. Similarly any other chemical group can be used in the context of the present invention, adapting accordingly the reactive group on the polymer and the chemically blocking reagent for the matrix.

In addition, the present invention provides a tool to detect the presence of a virus or bacteria, in a sample.

According to the present invention at least one aptamer is used in the detection assay.

In a specific example for the "single aptamer assay", the kit comprises:
(a) an aptamer bound to a coated matrix and (b) a biotinylated or non biotinylated ds-DNA associated with a succinimidyl group. The kit optionally further comprises related reaction and washing buffers.

The kit may comprise also a positive control antigen.

In addition, the kit may comprise a T7 RNA polymerase enzyme, NTPs, biotinylated UTP and related buffers.

The kit may further comprise biotinylated RNA bound to a capture matrix, such as beads.

The kit may further comprise SA=HRP/AP solution.

The kit may further comprise HRP/Alkaline Phosphates substrate buffers and stoppers.

In accordance with the "single aptamer assay" embodiment of the invention, the following assay is an example for the assay which may be performed using the kit of the invention:

1. A test sample is added to a pre-coated matrix-aptamer complex. The sample is incubated with the pre-coated matrix-aptamer complex for about 30-60 min at room temperature (RT) followed by magnetic separation and washing (×5 with PBS/EDTA 1 mM/Tween-20 0.01%).

2. biotin-ds-DNA associated with a Succinimidyl group is added and incubated for about 30 min at RT followed by magnetic separation and washing (×5 with PBS/BSA 2%/Tween-20 0.01%).

3. Optionally, a T7 RNA polymerase reaction is performed by adding the components required for the reaction such as: T7 RNA polymerase enzyme, NTPs, biotinylated UTP and related buffers for 60 min at 37° C. followed by magnetic separation and transfer of the RNA to the capture tube.

4. SA=HRP/AP solution is added for an incubation of 30 min at RT followed by washing (×5 with PBS/BSA 2%/Tween-20 0.01%).

5. The related substrate solution is added for 5-10 min at RT followed by measurement of absorbance or fluorescence (such as TMB as chromophore for HRP, pNPP as chromophore for AP, Attopose as fluorophore for AP).

Two additional tests may be performed in parallel, the first assay is a negative control assay including only the buffers and washing solutions and the second assay is a positive control which contains a pre-determined known amount of antigen in the sample.

If the target antigen (Ag) is present in the tested sample, it will induce Succinimidyl-dsDNA complex binding to the magnetic beads via the Aptamers Ag complex. This will allow the binding of the SA=Enzyme to the biotinylated DNA and eventually induce a measurable signal (with and without additional RNA transcription).

If the antigen is not present in the sample, then there will be no signal detected in both negative control and sample tubes.

This experiment may provide the following:
1. A qualitative (yes or no) test—by comparison with a negative control tube.
2. Semi-quantitative test—by adding control samples that contain low and high antigen concentration.
3. Quantitative test—by adding control wells that contain full Ag concentration standards.

Figure 7:
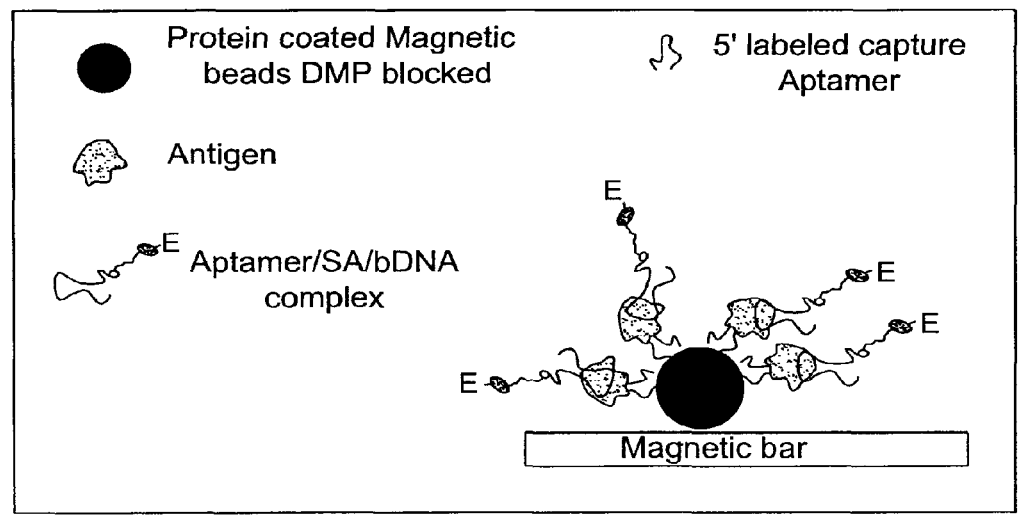
FIG. 7 shows a schematic illustration of the "dual aptamer assay".

According to some aspects of the invention, it is appreciated that when the target is a cell surface antigen, the first binding agent (being bound to the matrix) is used for the identification of the target cells, and a second binding agent is used for identification of a subpopulation comprising for example a surface antigen. FIG. 7 shows a schematic illustration of the "two binding agents assay". For example, two aptamers may be used in the detection assay. In such case each of the aptamers may be directed to a different target protein or to a different epitope on the same protein. The dual aptamer detection assay may be suitable for example for the detection of a cell surface molecule, or for the identification of specific cell populations or pathogens.

According to some embodiments, the present invention provides a kit for detection of an antigen using a "two binding agents assay". This assay may be used to identify an antigen which is associated with other antigens, in the biological sample, such as cell surface antigens and complexes.

Thus, for example in the "two binding agents assay" embodiment, the ds-DNA may be bound to a streptavidin associated aptamer complex, directly to an aptamer. In some specific embodiments, the ds-DNA may be bound to a streptavidin associated aptamer complex to a secondary related antibody For example in the "two binding agents assay", the kit may comprise:
a. an aptamer bound to a coated matrix; and
b. a second Aptamer or Aptamer/SA associated with a biotinylated ss-DNA or a ds-DNA chain in solution. The kit optionally further comprises related reaction and washing buffers.

The kit may further comprise a positive control antigen.

The kit may further comprise a T7, SP6, or M13 RNA polymerase enzyme, NTPs, and optionally, related buffers.

The kit may further comprise Biotinylated NTPs.

The kit may further comprise biotinylated RNA bound to a capture matrix such as for example beads.

The kit may further comprise SA=HRP/AP in solution.

The kit may further comprise HRP/Alkaline Phosphates substrate buffers and stoppers.

It is appreciated that according to the invention, any fluorometric substrate may be used in accordance with the invention, for example, the color based Alkaline Phosphate substrate pNPP, a fluorophor substrate such as AttoPhos®, AP Fluorescent Substrate, Adamantyl-1,2-dioxetane phosphates or Lumi-Phos 530. The use of such fluorescence substrates will allow increasing the assay sensitivity, for the detection of as low as $10^3$ Ag copies in the assay tube.

The measurement of the fluorescence in accordance with the invention may be performed with any fluorescence measurement device including Hand held, portable fluorometer devices such Invitrogene's—"Qubit® Fluorimeter", Topac Inc.'s—"picofluor" and Promega's—"TBS-380 Mini Fluorometer".

These devices are highly sensitive and can detect fluorescence and illumination at vireos excitation and emission wave lights. The use of such devices will allow performing the assay at point of care (POC).

EXAMPLES

Example 1: Preparation of Aptamers Associated with a Matrix and Having Blocked $NH_2$ Groups A) Use of Streptavidin (SA) DynaBeads (DB) and Biotinylated-Aptamers Streptavidin DynaBeads M-280 (Invitrogene) were washed with Tris/EDTA Buffer (TE) and incubated with commercial $C_{12}$-biotinylated aptamers, according to manufacturer's instructions.

At the end of the incubation period, biotin, at double molar ratio to the beads capacity was added, to block any free SA sites. Following washings with TEN (TE with 1M NaCl) and phosphate buffered saline (PBS) buffers, the DB-SA-aptamer complexes were kept at 4° C. in PBS.

For the blocking of all primary $NH_2$ groups, on the SA surface, the DB-SA-aptamer complexes were incubated with 5 mg/ml dimethyl pimelimidate (DMP) cross linker (Pierce) in Borate buffer, as directed by the manufacturer, for overnight at RT. It is noted that citraconic anhydride (CA) can also be used for the same purpose—see below).

To block unbound DMP reactive sites, the beads were washed (Borate buffer), and incubated in borate buffer which contains Tris (100 mM) for 6 h at RT. Following washings with PBS buffers, the prepared DMP/DB-SA/Aptamers were kept at 4° C. in PBS/EDTA.

B) Use of BSA Coated DynaBeads and SH-Aptamers—Association Via Cross-Linking

DynaBeads M280 Tosylactivated (10 mg) were coated with BSA according to manufacturer's instructions, using excess BSA. Blocking of the Tosylactivated residues on the beads is done by using Tris.

DB-BSA were incubated for 1 h at RT with Sulfo-Succinimidyl-4-(N-maleimidomethyl) cyclohexane-1-carboxylate (s-SMCC) or Sulfo-Succinimidyl-4-(p-maleimidophenyl) butyrate (s-SMPB) cross linkers (50 µl of 20 mM in DMSO into 500 µl of 1 mg beads in PBS/EDTA), followed by 5 washes in PBS/EDTA.

In parallel, SH-aptamers were obtained by either treating the tiol-Aptameres with DTT (10 mM, 30 min at RT), or by creating a SH-Group on the $NH_2$-aptamers as follows: 50 µl of the aptamer-$NH_2$ (200 mM) were incubated at RT for 45 min with 5 µl of N-Succinimidyl 3-[2-pyridyldithio]-propionate (SPDP) cross linkers (20 mM) in a total volume of 50 µl in PBS/EDTA. 5 µl of DTT 1M was added and samples were incubated for 30 min at RT. Excess SPDP and DTT were removed by using 1 ml Sephadex G-25 dray column.

Immediately 50 µl of the aptamer-SH were added to the activated DB-BSA (5 mg beads in 200 ul of PBS/EDTA) and incubated for 2 h at RT.

Acetyl-Cys (100 µl, 50 mg/ml in PBS-EDTA1 mM buffer) was added and incubated for 6 h at RT (for blocking any remaining N-maleimidomethyl reactive groups, of the cross-linker).

Alternatively, the BSA coated beads were incubated with the Aptamer-$NH_2$ as describe above, in the presence of 25 µl of DMP cross-linker (5 mg/ml) over night at RT, followed by at least 6 h incubating with 0.2M Tris (pH-7.4).

After three washings with PBS/EDTA and additional two washings with 150 mM phosphate buffer pH=9.0, 250 µl of citraconic anhydride 20 mM in 150 mM phosphate buffer ph=9.0 were added and samples were incubated overnight at RT. Samples were washed five times with PBS/EDTA and kept at 4° C. in PBS/EDTA.

Alternatively, after three washings with PBS/EDTA and additional two washings with Borate buffer, the aptamer associated beads were incubated with 50 µl of 5 mg/ml DMP over night at RT in a total volume of 300 µl in Borat buffer. Samples were washed five times with PBS/EDTA and kept at 4° C. in PBS/EDTA C) Preparation of Biotinylated ds-DNA Attached to Succinimidyl Ester ('b-ds-DNA-SE")

Figure 8:
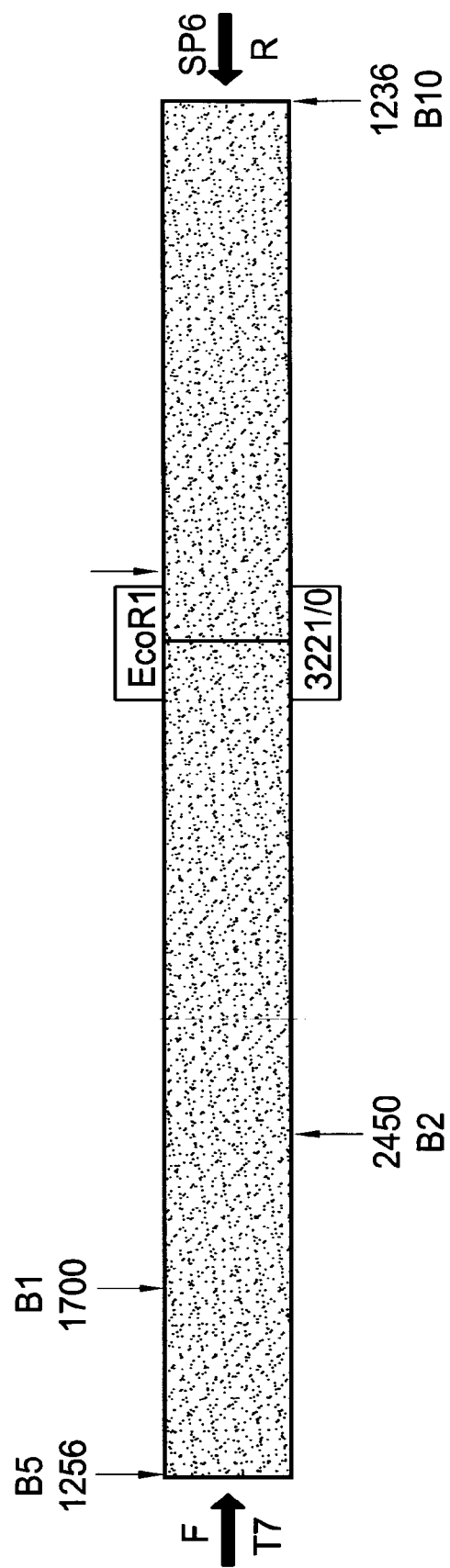
FIG. 8 shows a plasmid carrying the Hepatitis B scrambled sequence.

A plasmid carrying the Hepatitis B scrambled sequence was prepared by fishing out the DNA from HBV plasmid PadwHTD (Giladi H, Ketzinel-Gilad M, Rivkin L, Felig Y, Nussbaum O, Galun E. *Small Interfering RNA Inhibits HBV Replication in Mice.* Molecular Therapy, 8 (2003):769-76) and inserting it into pGMT-eazy, to receive Plasmid pGM-HBD (FIG. 8).

Associated Forward Primers:

```
                                     (SEQ ID NO. 1)
T7 - 5'-TAATACGACTCACTATAGGG-3'

(SEQ ID NO. 2)
B5 - 5'-CCTCTGCCGATCCATACT GCGGAAC-3'

(SEQ ID NO. 3)
B1 - 5'-GGAGGCTGTAGGCATAAATTGGTCTGCGC-3'
```

Associated Reveres Primers:

```
                                     (SEQ ID NO. 4)
SP6 - 5'-ATTTAGGTGACACTATAGAA-3'

(SEQ ID NO. 5)
B10 - 5'-ATGCGCTGATGGCCTATG G-3'

(SEQ ID NO. 6)
B2 - 5'-CCCGAGATTGAGATCTTCTGCGACGCGGCGATTGAGACC-3
``` pGM-HBD was submitted to PCR as follows: 1× Pentium-Taq Buffer (Invitrogen), 1× Pentium-Taq MgCl solution, 200 µM each dNTP, 50 µM biotinylated-dCTP, 50 pm of each primer (SP6/T7), 5 ng Template and 1 µl of Pentium-Taq, in 100 µl H2O.

If not state otherwise, the forward primer used was Tiol-$C_{12}$-T7 primer (Amine—$C_{12}$-T7 or $C_6$ primers can also be used).

PCR instrument program was designed according to the Pentium-Taq manuals for a PCR product of 3.5 Kb.

The Tiol labled biotinylated PCR products were pooled, treated with 50 mM DTT for 30 min at RT and DNA-SH was cleaned on MEGAquick-spinE-PCR extraction column or by employing 1 ml Sephadex G-25 dray column (or equivalent). To add a succinimidyl ester group, the biotinylated ds-DNA-SH was incubated with sSMPB/sSMCC cross linker (50 mg/ml, Pierce) for 30 min at RT. biotinylated ds-DNA—succinimidyl ester reagent (b-DNA-SE) was purified by Et-OH precipitation or by employing 1 ml Sephadex G-25 dray column. DNA-SE was re-suspended in PBA/EDTA contains PVP20 mg/ml.

It is noted that any other cross linkers that will create an Amine reactive group at the DNA 5', such as Maleic Anhydride can be used.

D) Preparation of Streptavidin-b-aptamer Attached to ds-DNA-SE

Streptavidin (SA) was incubated with biotinylated aptamers at a molar ratio of 1:4 (1 nm: 4 nm) in a total volume of 80 µl TEN buffer (TE with 1M NaCl), for 30 min at RT. Biotin, 2 nm in 20 µl TEN, were added and incubated for 30 min at RT (To block free SA sites).

SA-aptamer complex was cleaned on a sephadex G-25 super fine 5 ml column. Each 25 µl of the above (about 250 pm SA) were incubated with about 20 µg of b-DNA—SE in PBS/EDTA (1 mM), in a total volume of 100 µl, for 1 h at RT. 10 µl M Tris was added (To block the un-bound SE groups) ad incubated for 1 h at RT.

Aptamer-SA-bDNA complexes were diluted 1:10 in PBS 0.01% tween 20.

100 µl reagent was used per assay sample.

E) Preparation of aptamer Directly Attached to ds-DNA-SE ds-DNA-SE was incubated with $NH_2$-aptamers at a molar ratio of 2:1 in a total volume of 50 µl PBS/EDRA 1 mM for 120 min at RT. Un bound reactive SE groups were blocked with Tris (0.2 M) for 3 h at RT in total volume of 100 ul.

Aptamer-bDNA complexes were diluted 1:10 in PBS 0.01% tween 20.

100 µl reagent was used per assay sample.

F) Preparation of IgG/b-DNA Complex

IgG, 50 µl of 2 µg/ml, were incubated with 25 µg DNA-SE for 1 h at RT in a total volume of 100 µl PBS/EDTA 1 mM. Tris 1M was added (10 µl) (to block un-bound SE) and incubated for 1 h at RT.

IgG-bDNA was diluted 1:10 in PBS/tween 20 (0.01%) and 100 ul were used for each assay sample.

Example 2: Validation of the Enhancement Capability of b-DNA-SE

The Legend max human TNF ELISA kit (BioLegend) was used as a commercial ELISA kit.

1 ml of anti-TNFα antibodies solution (Legend max human TNF ELISA kit—BioLegend) was reacted with b-DNA-SE as described above, thereby obtaining modified anti TNFα antibodies. Per each assay, 110 µl of IgG-bDNA-SE were used.

The assay was performed in 3 different versions [A, B and C] to allow comparison:

A) According to Manufacturer's instructions.

B) According to Manufacturer's instructions except that instead of the secondary anti-TNFα Ab solution provided in the kit, the modified IgG-bDNA was added.

C) As in (B) except that after the addition of the modified IgG-bDNA a step of T7 RNA polymerase reaction was preformed, with the addition of Biotin-UTP. The biotinylated RNA was loaded on Avidin-magnetig beads (DB-M280-SA), followed by washing with the washing solution and the addition of SA-HRP. Beads were washed with the Kit's washing solution and the kit's substrate was added.

Figure 9:
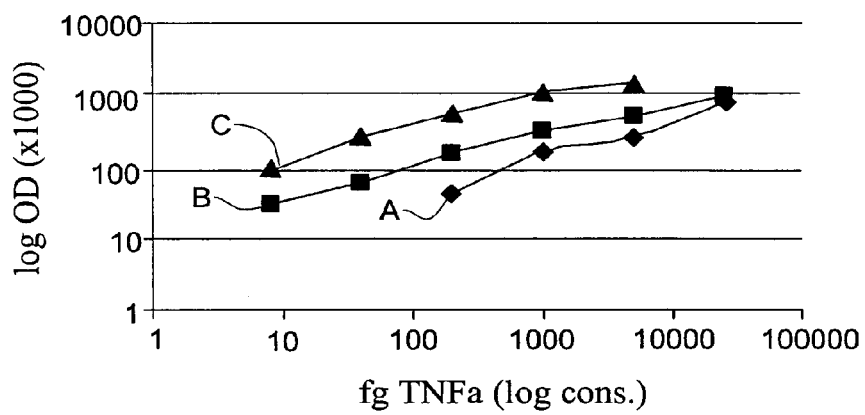
FIG. 9 is a graph showing the detection of TNF-α by (A) unmodified TNF-α antibody (B) TNF-α antibody attached to a b-DNA-SE group (C) TNF-α antibody attached to a b-DNA-SE group and using an additional step of T7 RNA amplification.

Results:

FIG. 9 clearly shows that the modified Abs (B) gave a result which is about one and a half logs more sensitive than the unmodified antibodies (A). T7 RNA amplification (C) enhanced the signal, increasing the sensitivity by at least about one more log. In all 3 assays the background level was very low if any.

These experiments demonstrate the ability of the multi biotinylated DNA to highly increase ELISA sensitivity, with the possibility of further increasing sensitivity by employing the RNA amplification techniques. This assay is reaching a sensitivity of below $5 \times 10^{e5}$ TNF molecules per assay, using a spectrophotometer.

Example 3: Detection of PDGF-BB Using Atamers

The following Aptamer-based assay was developed for the monitoring of platelet-derived growth factor B-chain homodimer antigen (PDGF-BB) in PBS FCS human serum and Plasma.

Methods:

Reagents:

RayBio Human PDGF-BB ELISA Kit [Cat#: ELH-PDGFBB-001] and its reagents were used as a reference for the assay.

The aptamers for platelet-derived growth factor B-chain homodimer antigen PDGF-BB (Sigma) were designed as follows as described (Yuan Li, et al. *Ultrasensitive Densitometry Detection of Cytokines with Nanoparticle-Modified Aptamers*. Clinical Chemistry 53(2007):6; Yong Huang, et al. *Electrochemical immunosensor of platelet-derived growth factor with aptamer primed polymerase amplification*. Analytical Biochemistry 382 (2008): 22).

```
PDGF-BT-1:
                                    (SEQ ID NO. 7)
biotin-5'-GCGATACTCCACAGGCTACGGCACGTAGAGCATC

ACCATGATCCTG-3'
```

```
SCREM-BT-1:
                                    (SEQ ID NO. 8)
biotin-5'-GCGATACTCCACAGCTGACGGCACGGTAAGCATCA

CCATGATGTCC-3'
```

```
PDGF-BT-2:
                                    (SEQ ID NO. 9)
biotin-5'-GCAGTTACTCAGGGCACTTGCAAGCAATTGTGGTC

CCAATGGGC TGAGTAT-3'
```

DB-SA/Aptamer was prepared as described above, employing the aptamer PDGF-BT-2 and its scrambled form SCREM-BT-1.

Aptamer-SA-bDNA was prepared as described above, employing the aptamer PDGF-BT-1 or SCREM-BT-1.

Anti-PDGF-BB-bDNA-SE complex was prepared as described above.

Assay Construction:

DB-SA carrying the PDGF-BT-2 or SCREM-BT-1, were washed three times and resuspended in PBS/Tween-20 (0.01%).

Recombinant PDGF-BB was added (100 µl of 1 pg/ml, 100 fg) in the same buffer or in fetal calf serum (FCS) 0.01% tween-20, and incubated for 1 h at RT while rotating. In a parallel assay, a sample of human-serum containing 0.01% tween-20 was added and incubated as above.

Antigen associated DB-SA with the attached aptamers were incubated with either PDGF-BT-1 or SCREM-BT-1/SA-bDNA-SE or anti-PDGF-BB-bDNA. After about 1 h incubation at RT, the complexes were washed ×3 with PBS/BSA/Tween and then SA-HRP (1:5000 in PBS/BSA/Tween buffer) was added and incubated for 30 min at RT.

The HRP labeled beads were washed ×5 with PBS/BSA/Tween, and substrate (100 µl) was added to the pellets. The reaction stopper solution was added within 2-5 min, beads were removed and supernatants were evaluated at 450 nm, employing Tecan fluorometer/spectrophotometer.

Figure 10A:
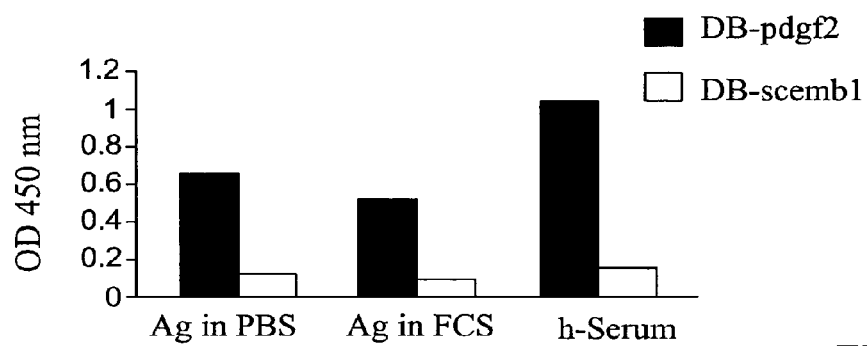
FIGS. 10A and 10B are bar graphs showing the detection of recombinant PDGF-BB in PBS and in FCS and of native PDGF-BB in human serum using PDGF-BT-2 aptamer attached to the matrix (10A) signal detection using bDNA-SE (10B) Employing a dual aptamer assay by using PDGF1 aptamer attached to SA-b-DNA for detection.

Results:

The ability of the PDGF2 aptamer to recognize and bind recombinant and native PDGF-BB to the beads was studied by employing a rabbit anti PDGF-BB antibody which carries a bDNA (FIG. 10A).

It was found that a relatively high signal was detected when a PDGF-BB specific aptamer (PDGF2) was associated with the beads. Low signal, if any, (under 0.15 OD) was detected when the scrambled aptamer was associated with the beads.

These results demonstrate the specific binding of the antigen, namely PDGF-BB, to the beads-aptamer complex.

The results in FIG. 10A also show the ability of the aptamer to bind the recombinant FDGF in serum environment (FCS), as well as to bind native FDGF-BB from human sera.

The RayBio Human PDGF-BB ELISA Kit has a sensitivity of 50 fg/assay, showing an average of 0.3 OD for 100 fg antigen, the amount of Ag used in the experiment. We have demonstrated that by associating to the antibody a large amount of Biotin, and therefore a large amount of HRP, the signal is strengthened thereby enhancing the assay sensitivity.

In addition, a second aptamer was used in order to introduce and bind SA-HRP-bDNA to the Ag/Beads complex.

Figure 10B:
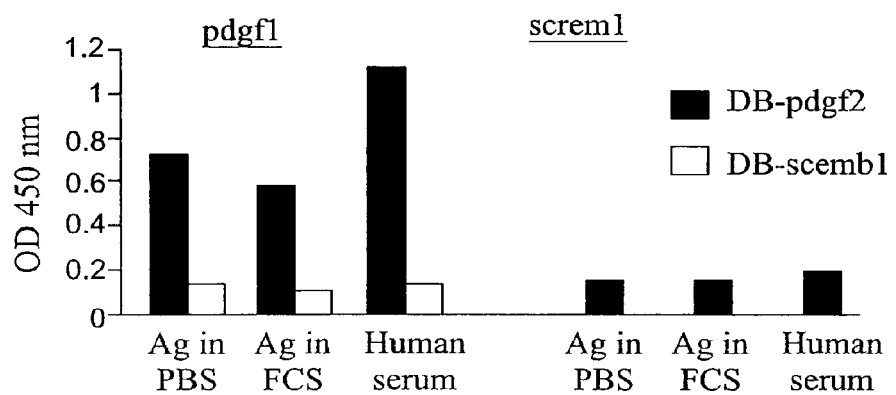

The results which are represented in FIG. 10B demonstrate the specificity of the second aptamer PDGF1 to the Ag, i.e. PDGF-BB (Left side), showing only low background, using the scrambled Aptamer screm1 as a second aptamer (right panel)

A relatively high signal, which implies a higher sensitivity, was observed when a large number of HRP molecules (about 250) were associated with the Aptamer/SA (or IgG) complex, via the attached biotinylated ds-DNA. As shown above, the scrambled aptamer failed to bind PDGF, either recombinant or native, to the beads.

Figures 11A, 11B:
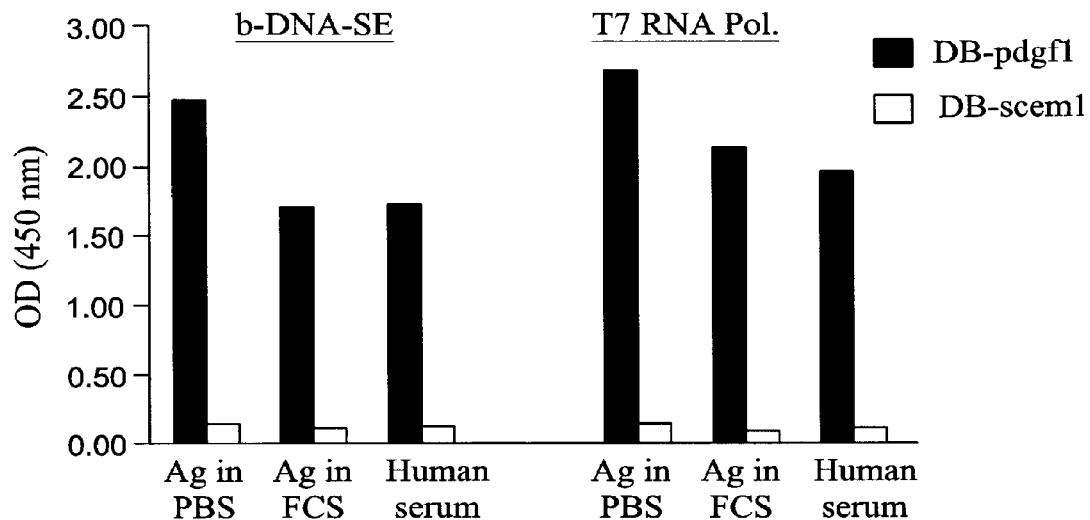
FIGS. 11A and 11B are bar graphs showing the detection of PDGF-BB in serum using PDGF-2 aptamer attached to the matrix, by different amplification methods (11A) b-DNA-SE (11B) a T7 RNA polymerase reaction. (1:10 of Ag).

Example 4: The Use of Aptamers and b-DNA-SE as a Tool for Antigen Detection and Quantitation—Comparison of Different Amplification Methods An assay, based on DB-Streptavidin aptamers and biotinylated-DNA-SE, was developed for the monitoring of PDGF-BB in PBS, FCS and human serum and Plasma.
Materials:
Using the same three aptamers for PDGF-BB as described above, DB-SA/aptamer complexes and b-DNA-SE was prepared as described above.
The DB-SA/aptamers complex was treated with DMP in order to block all primary $NH_2$ groups on the SA surface, as described above.
The experiments were performed using 1 pg of PDGF in b-DNA-SE assay and 50 fg in T7 RNA polymerase amplification assay.
Results:
The Succinimidyl Ester from the ds-DNA complex is capable of attacking and covalently binding primary $NH_2$ groups
Since the $NH_2$ groups on the Streptavidin (SA) associated with the beads are blocked by the addition of DMP, the only source for primary $NH_2$ groups in the complex is from the PDGF-BB antigen. Thereby ensuring a specific binding of the ds-DNA-SE only to the antigen, namely PDGF and eliminating any unspecific binding of the ds-DNA-SE to the beads.
Indeed, the results in FIG. 11 suggest that all the SA molecules on the beads carrying primary $NH_2$ groups are blocked, and that under the above conditions, there is no unspecific bindings of Ag to the beads/aptamers complex.
This was also evident when BSA was used as antigen instead of the PDGF-BB antigen.
In addition, as shown in FIG. 11A, the DNA-SE binds only to beads carrying the PDGF2 aptamers, and thus carrying the PDGF-BB and not to beads carrying the scrambled aptamer (scrm1).
Moreover, no background was detected neither when PDGF-BB was present in FCS nor in its native environment i.e. in human serum. These results indicate the specificity of the above described aptamer assay.
The assay described above also shows high sensitivity, in comparison with the RayBio Human PDGF-BB ELISA Kit.
The assay sensitivity can be increased, by performing the T7 RNA amplification step, as shown in FIG. 11B.
As shown in FIG. 11B, the T7 RNA amplification step increased the sensitivity compared to the b-DNA-SE assay by about 1.5 logs.
It is noted that while the RayBio Human PDGF-BB ELISA Kit has a sensitivity of 50 fm Ag (about 0.3 OD), the T7 RNA amplification step measured a signal of over 2.0 OD at the same Ag amount in the assay, showing a potential to about 2-3 logs less Ag than with the kit.

Example 5: The Use of ss-DNA-SE and Branched-DNA Assay

Figures 12A, 12B:
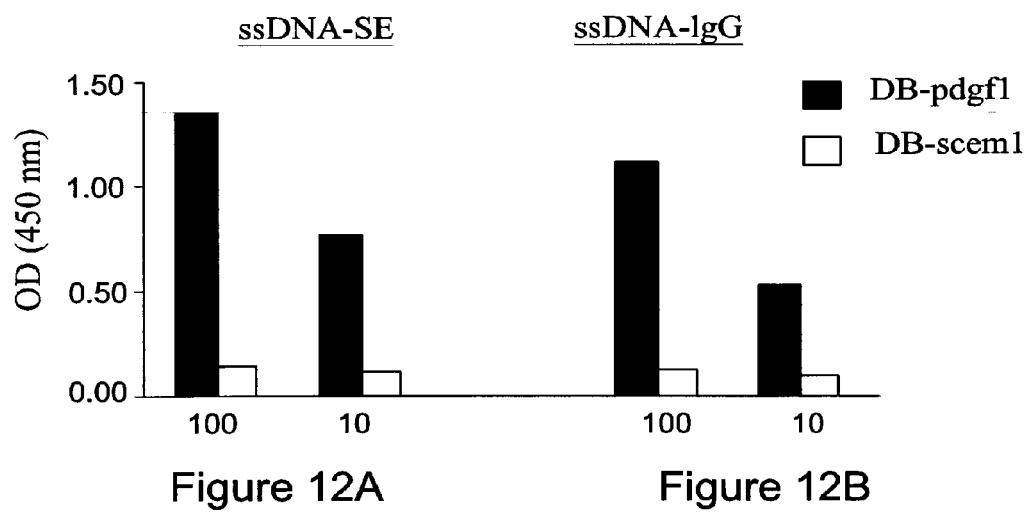
FIGS. 12A and 12B are bar graphs showing the detection of PDGF-BB with the branched DNA technology using (12A) ss-DNA-SE (12B) ss-DNA IgG.

In this example, an assay, based on DB associated aptamers and ss-DNA-SE and Branch-DNA assay, were developed for the monitoring of PDGF-BB in PBS.
Materials:
Using the same three aptamers for PDGF-BB as described above, DB-SA/aptamer complexes and b-DNA-SE were prepared as described above.
The DB-SA aptamers complexes were treated with DMP in order to block all primary $NH_2$ groups on the SA surface, as described above.
ss-DNA-SE was bound to anti-PDGF-BB as described in experiment 1.
Branch-DNA assay kit for HBV V-3.0 (VERSANT) was used according to the manufacturer's instructions, albeit, eliminating the "DNA capture" step.
After establishing the AP/DNA complex, PNPP substrate was added.
The experiment was performed using the indicated amounts of Ag in assay, as described in example 4.
Assays Samples and Results:
The Branched-DNA assay (which is originally used in the prior art to monitor and quantitate DNA and RNA) was adapted and found to be effective and sensitive for the determination and quantitation of a protein Antigen in the constructed assay, e.g. the detection of PDGF.
As described above, the presented results also show that the ssDNA-SE and the ssDNA-IgG complexes bind only to beads associated with the PDGF2 aptamer, and therefore to PDGF, and not to beads carrying the scrambled aptamer (scrm1), indicating the specificity of the assay (FIGS. 12A and 12B).

Figure 13A:
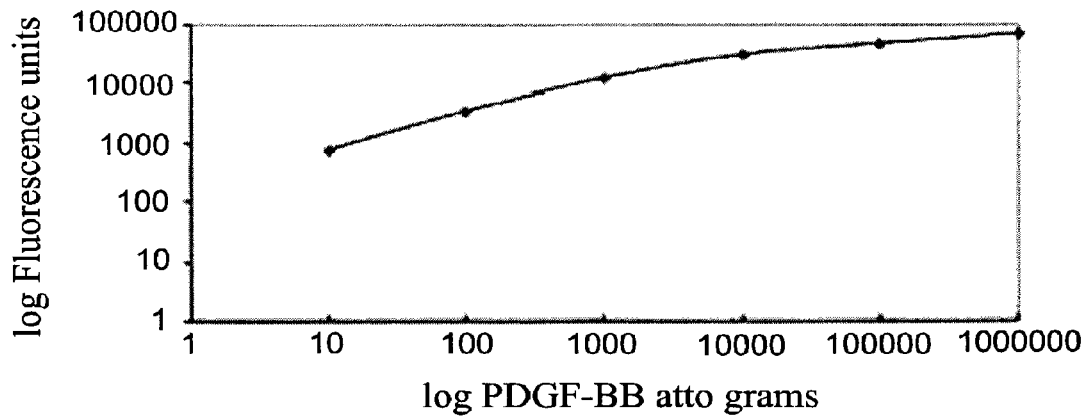
FIGS. 13A-13C are graphs showing the detection sensitivity of PDGF-BB antigen using the PDGF2 aptamer and b-DNA-SE by fluorometric substrate or chromogenic substrate (13A) AttoPhos® Alkaline phosphates fluorescent substrate system and a Tecan fluorometer (13B) AttoPhos® Alkaline phosphates fluorescent substrate system and a Qubit® Fluorometer (hand size) (13C) pNPP Alkaline Phosphatase chromogenic substrate.

Example 6: The Use of Fluorimetric Base Dye and the Qubit® Fluorometer for Measurements of BD-Aptamers and b-DNA-SE Based Ag Detection and Quantitation Assay AttoPhos Substrate is an Alkaline Phosphate fluorimetric substrate (ex.—430 nm/em.—560 nm). In this example the sensitivity of the constructed assay was studied, employing color base Vs flourimetric substrates (PNPP/AttoPhos).
The tested assay was based on DB-SA-aptamers and biotin-ds-DNA-SE, for detecting PDGF-BB, and using commercially available SA=AP (alkaline phosphates) complex.
Reagents and Experimental Methods:
PDGF-BB antigen, DB-SA/PDGF2 aptamer, and b-DNA-SE were prepared as described in the example above. The DB-SA/Aptamers complex was treated with DMP in order to block all primary $NH_2$ groups on the SA surface, as described above. All other experimental procedures were performed as described above.
The assay was performed as described above employing SA=AP, followed by the related substrate addition and signal readings.
For Qubit® Fluorometer readings, the samples were first read by Tecan fluorimeter and then transferred to 0.5 ml tube for Qubit® Fluorometer readings. Qubit® Fluorometer calibration (employing the Quant-iT™ DNA Assay setting), was performed using the "no Ag" sample as "standard #1, and the 100 fg Ag as standard #2. Results are expressed at "related DNA values" in ng/ml.
Results:
The results in FIGS. 13A and 13C clearly demonstrate that using the Atto-Phose substrate higher sensitivity of the assay is achieved, about 2 logs more sensitive than with the PPNP substrate (10 ag Ag Vs 1 fg Ag, correlated to $4\times10^2$ Vs $4\times10^4$ Ag molecules in the assay).

Figure 13B:
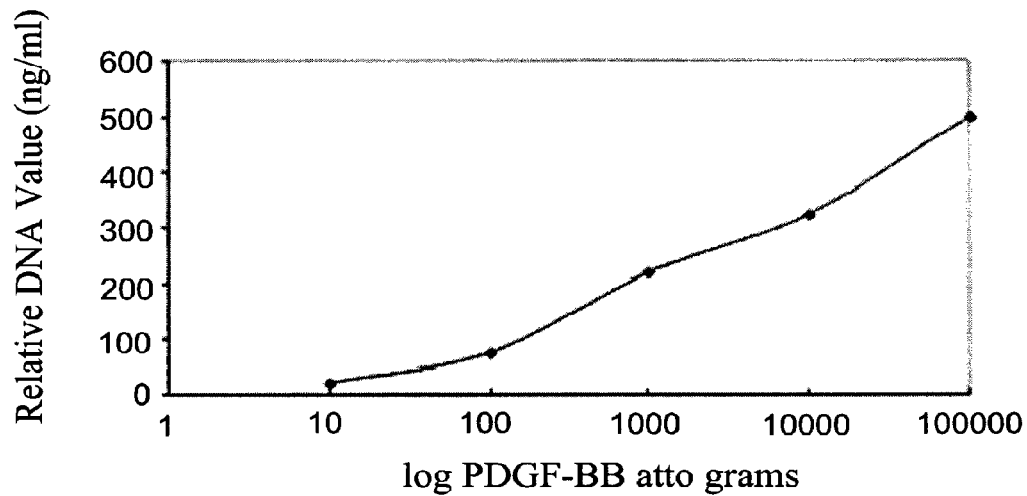
Figure 13C:
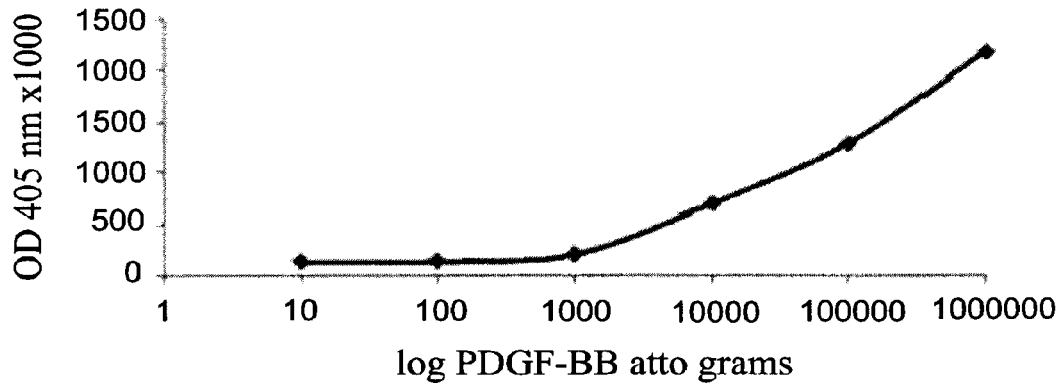

The results also demonstrate that the Qubit® Fluorometer can be use as a hand size fluorometer in the assay of the invention (FIG. 13B). The results demonstrate that the Qubit instrument is suitable for Atto-Phose fluorescence readings, with sensitivity similar to the Tecan fluorometer.

Example 7: The Use of DB-BSA-Aptamers as a Tool for Antigen Capture and b-DNA-SE for Ag Detection and Quantitation Cytomegalovirus (CMV) disease is a major life-threatening complication in recipients of blood and bone marrow transplants (BMTs). CMV may cause deadly interstitial pneumonitis, esophagitis, gastritis, colitis, hepatitis, fever, leukopenia, and a severe wasting syndrome. Identifying the CMV infection, combined with ganciclovir/immunoglobulin (IVIg) therapy, is the most effective preventive therapy in BMT patients. Therefore, patients are undergoing surveillance tests (cultures, serology, and antigen detection) of blood and other body fluids to detect evidence of CMV activation.

An assay, based on DB-BSA-Aptamers and biotinylated-DNA-SE, was developed for the monitoring of the Cytomegalovirus gB surface glycoprotein (CMV-gB) in PBS, and human serum and Plasma.

Materials:

Aptamers for CMV-gB were designed as follows as described (Wang, J. et al *In vitro selection of novel RNA and DNA ligands that bind human cytomegalovirus and block viral infection*, RNA, 6, (2000):571-583, 2000).

```
gB1
                                        (SEQ ID NO. 10)
Tiol-C12-5'-TTACGGTCACCTTACCCCTGGGTGTGCTCT TC

CCGGTGGG-3'

SCREM-1:
                                        (SEQ ID NO. 11)
Tiol-C12-5'-GCGATACTCCACAGCTGACGGCACGGTAAGCAT

CACCATGATGTCC-3'
```

DB-BSA/Aptamer was prepared as described above, employing CA for the matrix primary $NH_2$ blocking.

DNA-SE was constructed as describe above.

Assay Construction I:

DB-BSA carrying the different aptamers were washed, re-suspend in PBS/Tween-20 (0.01%) and then reformed into a pellet. To a pellet of 0.5 mg beads, recombinant CMV-gB or PDGF-BB were added (100 µl 10 pg/ml) in PBS/Tween-20 (0.01%) and 1% BSA and incubated for 1 h at RT with rotating.

Samples were washed five times with PBS-EDTA-Tween and 100 µl b-DNA-SE was added and the samples were incubated for 60 min at RT.

Following three washings with PBS—Tween and additional two washings with PBS-BSA-Tween, 100 µl of SA-HRP (1:5000) were added and incubated for 30 min at RT.

Samples were washed five times with PBS-BSA-Tween and then 100 µl TMB (TMB One-Step Substrate Reagent, Thermo Scientific) were added and incubated for 10 min at RT.

Reaction was stopped with 100 µl Stop solution and the samples were read at 450 nm within 30 min.

Figures 14A, 14B:
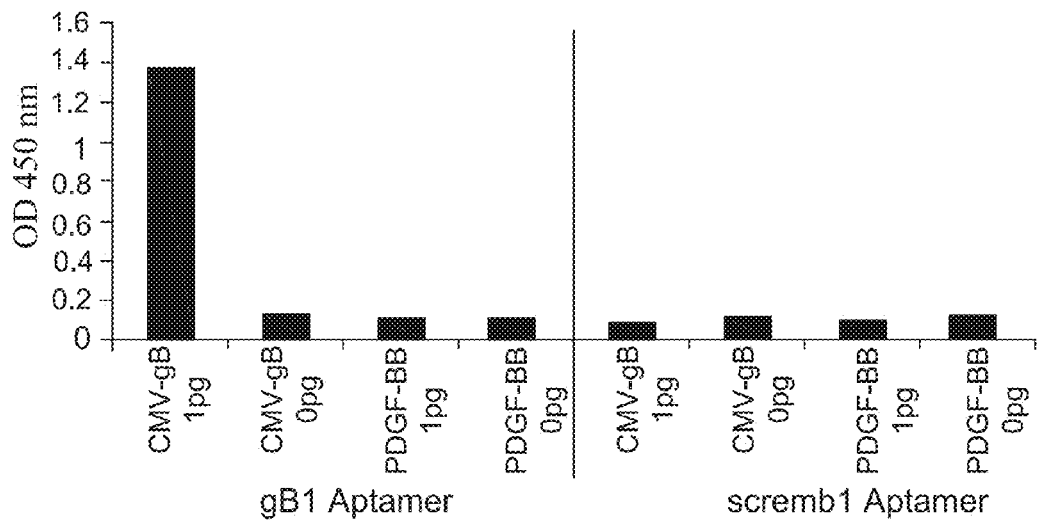
FIGS. 14A and 14B are bar graphs showing the specificity of detecting recombinant CMV-gB antigen using (14A) the CMV-gB1 aptamer (14B) scrambled aptamer.

Results:

As shown in FIG. 14, the blocking of the $NH_2$ groups of the BSA associated beads with CA was effective, therefore the only source for primary $NH_2$ groups in the system is the bound Ag.

As shown in FIG. 14, the b-DNA-SE binds only to beads carrying the gB1 aptamer, in the presence of the CMV-gB antigen (14A) and not bind to beads carrying the scrambled aptamer (scrmb 1, 14B).

In addition, signal is obtained only with the CMV-gB antigen, while only background signal is obtained with the PDGF-BB Antigen. These results indicate that the gB1 aptamer is specific to the CMV-gB antigen and does capture the PDGF-BB Antigen, or the buffer associated BSA.

Assay Construction-II:

DB-BSA/Aptamer (pellet of 0.5 mg beads) prepared as described above were re-suspended in cultured CMV (1.4× 10e4 PFU) spiked into either PBS/BSA buffer or into human serum (100 µl). Following 60 min incubation at RT with rotation, samples were washed five times with PBS-EDTA-Tween and 100 µl b-DNA-SE was added. The samples were incubated for 60 min at RT, and then washed three times with PBS—Tween and twice with PBS-BSA-Tween.

100 µl of SA-HRP (1:5000) were added and the samples were incubated for 30 min at RT. Samples were washed five times with PBS-BSA-Tween. Then, 100 µl TMB were added and the samples were incubated for 10 min at RT. Reaction was stopped with 100 µl Stop solution and the samples were read at 450 nm within 30 min.

Figure 15:
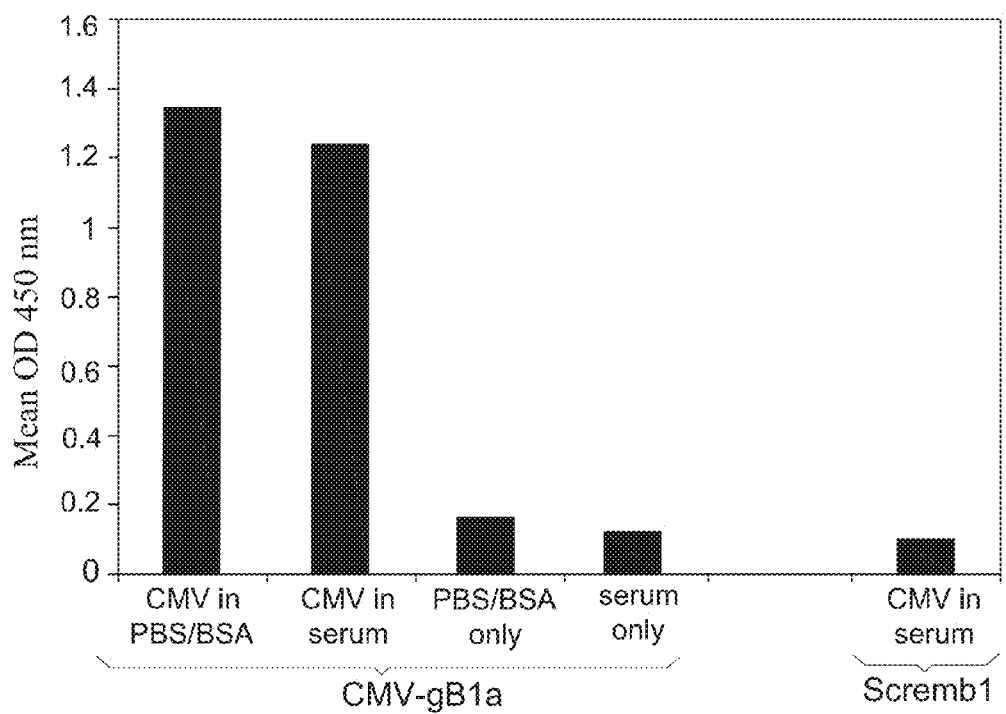
FIG. 15 is a bar graph showing the specificity of detecting cultured CMV (1.4×10e4 PFU) spiked into either PBS/BSA buffer or into human serum using the CMV-gB1 aptamer.

As shown in FIG. 15, the b-DNA-SE reagent binds only to beads associated with the gB1 aptamer in the presence of the cultured CMV, and not to beads associated with the scrambled aptamer.

The gB1 aptamer did not bind any protein component in the PBS/BSA buffer or in the tested human serum.

It is noted that another CMV antigen suitable for detection in accordance with the present invention is the early viral matrix structural protein pp65 in a subject's leukocytes.

The detection assay of the invention is suitable to determine few leukocytes carrying the pp65 on their surface, in patient's blood sample, without the need for using fluorescence microscope or FACS techniques. Using anti leukocytes aptamers bound to magnetic beads, leukocytes are separated and concentrated from whole blood sample. Adding a second biotinylated aptamer, which is directed against the pp65, allows the binding of the streptavidin ds-DNA. First amplification occurs as there are several hundred to several thousand copies of pp65 per cell. Second amplification occurs during the T7 RNA polymerase reaction (about 2 logs of bound ds-DNA). Without wishing to be bound by theory, one infected cell (in 0.1-1.0 ml of whole blood sample) may induce about $10^5$ RNA copies for bRNA reaction, which is sufficient for detection.

Example 8: Capture and Quantitation of Listeria Bacteria by Two Aptamers, Employing DB-BSA-Aptamers and b-DNA-SE An assay, based on DB-BSA-ptamers and b-DNA-SE, was developed for the monitoring and quantitation of the Listeria bacteria in PBS and in swabs.

Reagents:

Aptamers for Listeria were designed as follows as described in patent application US 20090203028.

Ap03:

(SEQ ID NO. 12)

NH$_2$-C$_{12}$-5'-ATCGATGATCTGGTCGCCGTAACACTACCCACATAT

ACGACCAGG-3'

Ap08:

(SEQ ID NO. 13)

NH$_2$-C$_{12}$-5'-ATCCATGGGCGGAGATGAGGGGGAGGAGGGCGGGT

ACCCGGTTGAT-3'

Aptamer NH$_2$—C$_{12}$-SCREMB-1 was prepared as described above.

The b-ds-DNA-SE used in this Example was constructed as describe above.

DB-BSA/Aptamer preparation—Use of BSA coated DynaBeads and NH$_2$—C12-5'-Aptamers.

Dyna-Beads M280 Tosylactivated (10 mg) were coated with BSA according to Manufacturer's instructions, using excess BSA ("DB-BSA"). Blocking of excess BSA was done by adding Tris.

DB-BSA were incubated over night at RT with 50 μl of one or more of the three aptamer-NH$_2$ described above (200 mM), and 75 μl of DMP cross-linker (1 mg/ml), in a total volume of 300 μl in Borate Buffer.

Free primary HN$_2$-groups on the BSA were then blocked by the addition of 100 μl of DMP cross-linker (5 mg/ml in Borate Buffer) and let over night at RT Free active ends of the DMP were blocked with Tris as described above. Samples were washed five times with PBS/EDTA and kept at 4° C. in PBS/EDTA.

Assay Construction:

DB-BSA-aptamer preparations were washed, re-suspend in PBS/Tween-20 (0.01%) and aliquoted as needed. To a pellet of 0.5 mg DB-BSA-aptamer complexes, varying amounts of several Listeria strains were added (in 100 μl of PBS/Tween/BSA). The samples were incubated for 1 h at RT by applying constant rotation. Samples were then washed five times with PBS-EDTA-Tween and 100 μl of b-DNA-SE preparation were added and incubated for 60 min at RT.

Following three washings with PBS—Tween additional two washings with PBS-BSA-Tween, 100 μl of SA-HRP (1:5000) were added and incubated for 30 min at RT. Samples were washed five times with PBS-BSA-Tween and 100 μl TMB were added and incubated for 10 min at RT. Reaction was stopped with 100 μl Stop solution and samples were read at 450 nm within 30 min.

Figure 16A:
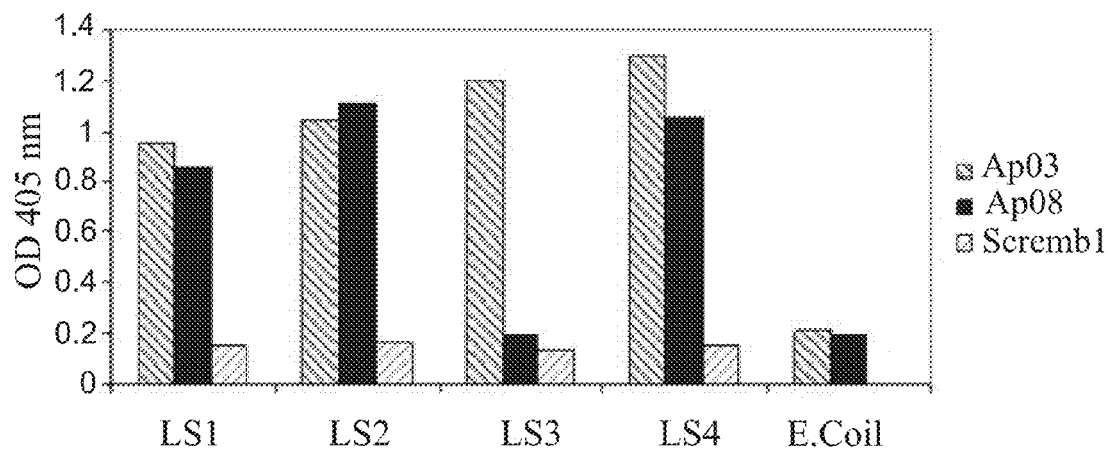
FIGS. 16A and 16B are bar graphs showing the detection of Listeria with aptamers (16A) specificity of the Ap03 and Ap08 aptamers to different Listeria strains (16B) concentration dependent studies of the Ap03 and Ap08 aptamers and of both aptamers on the same matrix in Listeria strain LS4.

Results:

As shown in FIG. 16A, the aptamer Ap03 recognized all 4 Listeria strains while the aptamer Ap08 did not recognize the LS3 strain. Both aptamers do not recognize the E. coli bacteria. The scrambled aptamer did not recognize any Listeria strains.

Figure 16B:
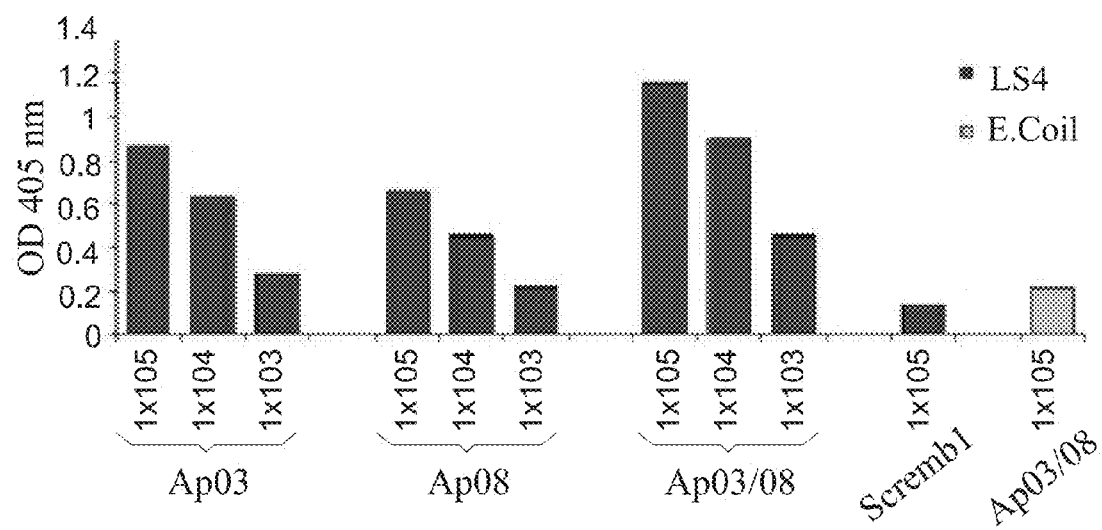

FIG. 16B shows that there is a synergistic effect between the two aptamers, Ap03 and Ap08 when attached to the same beads, resulting in a sensitivity of about $10e^3$ bacteria cells per system ($10e^4$ PFU/ml)

These results also show the efficiency of using DMP to covalently bind the aptamers to the BSA-DB, as well as its efficiently in blocking the primary NH$_2$ groups on the BSA associated beads.

Example 9: Capture and Identification of Listeria Bacteria by Two Aptamers Assay An assay, based on DB-BSA-aptamers and aptamer-SA-bDNA or aptamer-bDNA, was developed for the monitoring of the Listeria bacteria swab, re-suspended in PBS/BSA buffer.

Materials:

Aptamers were designed as described above (Ap03, Ap08, Scemb1). Preparation of streptavidin-aptamers attached to ds-DNA (Ap03, Scemb1) and aptamers directly attached to ds-DNA (Ap03, Scemb1) were preformed as described above.

Dyna-Beads M280 Tosylactivated coated with BSA and covalently bound to NH$_2$-AP08 were preformed as described above, employing DMA for both aptamers coupling and BSA NH$_2$ blocking.

Assay Construction:

DB-BSA-Ap08 preparations were washed, re-suspend in PBS/Tween-20 (0.01%) and aliquoted as needed. One colony of Listeria strain 4 (LS4) were collected as a swab with a cotton stick and the bacteria was re-suspended from the stick into 1000 μl of PBS/Tween/BSA.

To a pellet of 0.5 mg DB-BSA-AP08 complexes, 100 μl of bacteria preparation were added and incubated for 1 h at RT by applying constant rotation. Samples were then washed five times with PBS-EDTA-Tween and 100 μl of Aptamer-bDNA preparation were added and incubated for 60 min at RT.

Following three washings with PBS—Tween additional two washings with PBS-BSA-Tween, 100 μl of SA-HRP (1:5000) were added and incubated for 30 min at RT. Samples were washed five times with PBS-BSA-Tween and 100 μl TMB were added and incubated for 10 min at RT. Reaction was stopped with 100 μl Stop solution and samples were read at 450 nm within 30 min.

Figure 17:
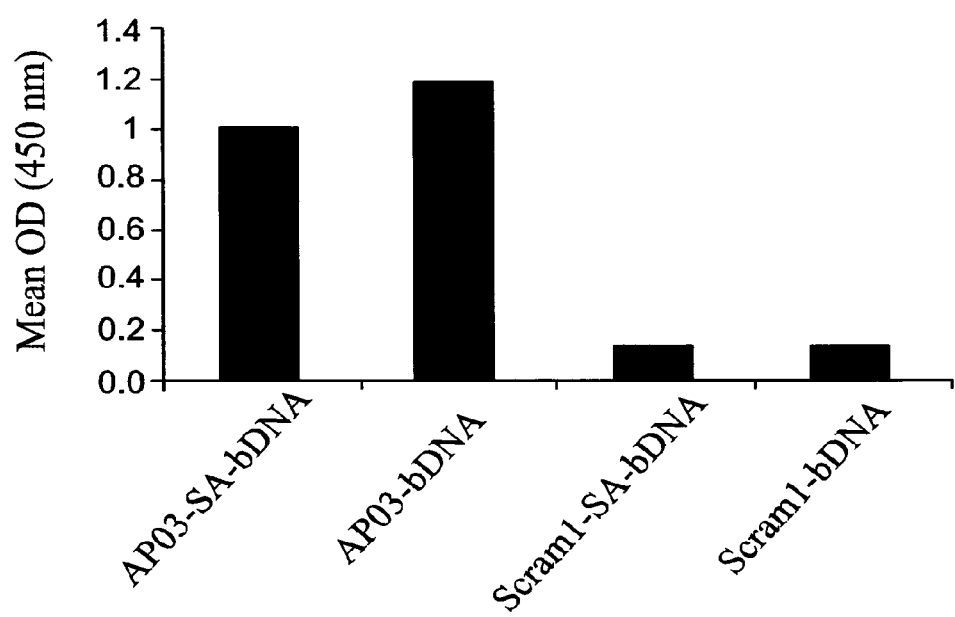
FIG. 17 is a bar graph showing the detection of Listeria bacteria (10e$^5$ PFU) by a dual aptamer assay using Ap03 and Ap08 aptamers.

Results:

As shown in FIG. 17, the aptamer Ap03 recognized the Listeria bacteria ($10e^5$ PFU), pre bound to the beads by the Ap08, while the scemb11 aptamer did not recognize the beads bound bacteria. These results were obtained with both aptamers-bDNA preparations, with or without SA, Example 10: A Rapid Detection Assay for Penicillin-Binding Protein 2' (PBP2')

Methicillin-resistant *S. aureus* bacteria have become a worldwide concern owing to their increasing frequency in hospitals, causing serious staphyloccal infections, including sepsis and endocarditis. Recent research suggests that in the identification of MRSA, it is more accurate to either directly detect the gene encoding the methicillin resistance determinant (mecA) or its product, penicillin-binding protein 2' and 2a (PBP2' and PBP2a), which is found in the cell membrane of MRSA (Barrett D, et al *Kinetic Characterization of the Glycosyltransferase Module of Staphylococcus aureus PBP2*. J. Bactrio. Mar. (2005) 2215-2217; Zeeshan M, et al. *comparison of different phenotypic methods of detection of methicillin resistance in staphylococcus aureus with the molecular detection of mec-a gene*. J. Coll. Physicians. Surg. Pak. 17 (2007):666-70). As nucleic acid hybridizaion and DNA amplification techniques such as PCR and real time PCR for detecting the mecA gene are expensive and technically demanding, simple and more inexpensive techniques are required for routine use. The MRSA cell has about 2000 PBP's per cell of which about 45% (900) are PBP2a and 25% (500) are PBP2' (Dabelsteen E, *Cell surface carbohydrates as prognostic markers in human carcinomas*. The Journal of Pathology, 179: 358-369).

The detection assay of the invention is suitable to determine Methicillin-resistant *S. aureus* presence (MRSA) in a biological sample by identifying the MRSA PBP2'/2a antigens. Rapid extraction of PBP2' from the bacterial membranes of MRSA is achieved by boiling the sample under alkaline conditions, followed by neutralization and centrifugation steps (Farra A, et al. *Role of outer membrane protein OprD and penicillin-binding proteins in resistance of Pseudomonas aeruginosa to imipenem and meropenem*. Int. J. Antimicrob. Agents. 31 (2008): 427-33.). This step, which destroys the bacteria, allows a safe working environment during the remaining steps of the procedure. Using anti PBP2 aptamers bound to magnetic beads, PBP2 is separated and concentrated from the biological sample (e.g. whole blood serum, plasma, and nasal or smear sample). This allows covalent binding of the added Succinimidyl-ds-bDNA to the PBP2. If required, an additional step of amplification can be performed using the T7 RNA polymerase reaction (about 2 logs of bound ds-DNA) as described above. A positive PBP2'/2a antigen test result indicates the presence of MRSA and enables the selection of an appropriate drug treatment.

Example 11: Bacterial Sepsis Assay—Detection of Procalcitonin Levels

Procalcitonin (PCT), a species-specific propeptide of calcitonin, is a protein of 116 amino acids with a molecular weight of 13 kDa. Under physiological conditions, PCT is produced and then cleaved by a specific protease to calcitonin and katacalcin in C-cells of the thyroid gland. However, strongly increased plasma concentrations of PCT were detected in patients with thermal injury, in children with bacterial Meningitis, and in patients with sepsis and severe infection (Maruna et al. *Physiology and Genetics of Procalcitonin* Physiol. Res. 49 (2000): 57-61; Dondana et. al. *Procalcitonin increase after endotoxin injection in normal subjects* J. Clin. Endocrinol. Metab. 79 (1994) 1605-1608).

In comparison to that of sepsis patients (1000-100000 pg/ml), the concentrations of PCT in the plasma of healthy blood donors were found to be very low (around 40 pg/ml). Due to these characteristics and to its very long half-life in the blood (25-30 hours), PCT is routinely used as a parameter for the diagnosis of severe bacterial and fungal infections and for mediator-directed therapy of sepsis (Maruna et al. *Physiology and Genetics of Procalcitonin* Physiol. Res. 49 (2000): 57-61; Dondana et. al. *Procalcitonin increase after endotoxin injection in normal subjects* J. Clin. Endocrinol. Metab. 79 (1994) 1605-1608).

The detection assay of the invention is suitable to determine low and high levels of PCT in patient's body fluid sample.

Using anti PCT aptamers bound to magnetic beads, PCT is separated and concentrated from whole blood, serum, plasma, nasal, smear, CSF or amniotic fluid sample. This allows the covalent binding of the added Succinimidyl-ds-bDNA to the PCT. If required, an additional step of amplification can be performed using the T7 RNA polymerase reaction (about 2 logs of bound ds-DNA) as described above. The values obtained from the assay are compared to a clinical reference table, driven from established clinical data and are correlated with the severity of bacterial sepsis.

Example 12: Detection of Cell Surface Associated Cancer Markers Using a "Two Aptamer" Assay Tumor development is usually associated with changes in cell surface glycolipids and proteins. These changes include incomplete synthesis, over expression and modification (terminal carbohydrate structures) of normally existing cell surface substances, as well as the expression of new genes that are not usually expressed in that specific cell type. These changes which differentiate the cell from normal (non-malignant) cells and characterize it as a tumor cell are identified as "cell surface cancer markers" (Olempska M, et al. *Detection of tumor stem cell markers in pancreatic carcinoma cell lines*. Hepatobiliary Pancreat Dis Int. 6 (2007)).

Cancer cells can "break away", "leak", or "spill" from a primary tumor, enter lymphatic and blood vessels, circulate through the bloodstream, and settle down to grow within normal tissues elsewhere in the body—metastasis. Most tumors and other neoplasms can metastasize, although in varying degrees. Therefore, tumor cells can be found in the blood circulation, as metastases as well as cancer cells associated with blood cells (Dabelsteen E, *Cell surface carbohydrates as prognostic markers in human carcinomas*. The Journal of Pathology, 179: 358-369).

The detection assay of the invention is suitable to determine even a few tumor cells in the blood circulation, by the identification of specific cell surface markers (presence, i.e. in a qualitative assay or amount in a quantitative assay) on the surface of selected cells, without the need for using a fluorescence microscope or FACS techniques. Using anti cell type directed aptamers bound to magnetic beads, the target cell is separated and concentrated from whole blood samples. Adding a second biotinylated aptamer, which is directed against the selected marker, allows the binding of streptavidin ds-DNA. First amplification occurs as there are many antigen marker copies per cell. Second amplification is occurs during the T7 RNA polymerase reaction (about 2 logs of bound ds-DNA). The values obtained from the assay are compared to a clinical reference Table, driven from established clinical data, for the determination of tumor cell existence.

Example 13: Kits for Simultaneous Detection of Several Antigens

The kits of the invention may also be used for simultaneous detection of several antigens in the same sample (for example a swab sample or a body fluid sample such as saliva, nasal secretion, blood, urine or feces). These simultaneous-multi-panel detection kits can be used in a "single aptamer assay" or a "dual aptamer assay" as described below.

Multi-"single aptamer assay": In stage-1 of the assay, different tubes are used each containing a different aptamer-beads complex, each aptamer-beads complex is directed against a single selected target. The remaining stages of the assay are performed as described above in the description of the "single aptamer assay". The tube which generates a fluorescence signal points to the presence of an antigen.

Some non-limiting examples include:

1) Hepatitis Kit: Suitable for the simultaneous detection of hepatitis A virus (HAV), hepatitis B virus (HBV), and hepatitis C virus (HCV) in a patient's serum sample. The importance of such a kit is based on the needs to identify the virus in the case of a patient with hepatitis symptoms, as there is a different treatment for each virus.

2) Meningitis Kit: Suitable for the simultaneous detection of Entero-virus, Herpes, CMV, Meningococcal, Pneumococcal, and Hib in patients' CSF sample. The importance of such a kit is based on the needs to rapidly identify Meningitis as having a bacterial or a viral base, as the severity of disease and mode of treatment differ according to the source of the infection.

3) Respiratory Kit: Suitable for the simultaneous detection of SARS, Influenza A+B, Avian Influenza, Adeno virus and Rhino virus in nasal wash and swabs. The importance of such a kit is based on the needs to rapidly identify the source of a respiratory infection, especially in the case of pandemic threat, in hospitals and clinics, as well as in air and sea ports.

4) Blood coagulation kit: Suitable for the simultaneous detection of a missing/mutant blood coagulation factor in a patient's circulation. The importance of such a kit is based on the needs to identify the source of a blood coagulation problem, to determine the appropriate treatment.

5) Tumor markers kit: Suitable for the simultaneous detection of soluble tumor markers in the patient's circulation. The importance of such a kit is based on the need to identify the existence and progress of a tumor within a patient's body, for rapid and appropriate treatment.

Multi "dual aptamers assays": In stage-1 of the assay, different tubes are used each containing a different aptamer-beads complex, each aptamer-beads complex is directed against a single cell type selected marker. In stage-2 of the assay a different biotinylated aptamer, directed against a specific antigen on the selected cells surface is added into each tube. The remaining stages of the assay are performed as described above in the description of the "Two aptamer assay". The tube which generates a fluorescence signal points to the presence of the cell type carrying the selected marker antigen.

Some non-limiting examples include:

1) Cell surface tumor markers kit: Suitable for the detection and identification of metastases by the simultaneous recognition of cells type and associated cell surface tumor markers, in a patient's circulation. Among these are: CD133 on colon cancer cells, Est-1 on pancreatic and thyroid carcinoma cells, p63 on myoepithelial cells, EPM-1 and EXO-1 on gastrointestimal tumors cells, TEMs on tumor endothelial cells and CD44+CD24-/low on breast cancer cells. The importance of such a kit is based on the need to identify the existence and progress of a tumor within a patient body, for rapid and appropriate treatment.

2) Methicillin-resistant bacteria kit: Suitable for the detection and identification of different methicillin-resistant bacteria strains, carrying the penicillin-binding protein 2 (PBP2), such as *Staphylococcus aureus, pneumococci, Escherichia coli* and *Pseudomonas aeruginosa*, and to distinguish between Methicillin-resistant *S. aureus* and borderline oxacillin-resistant *S. aureus* (Balslev U et al. *An outbreak of borderline oxacillin-resistant Staphylococcus aureus (BORSA) in a dermatological unit*. Microb. Drug Resist. 11 (2005):78-81.). According to this embodiment, the beads-associates aptamers are directed against each bacteria strain, and the biotinylated aptamer against a shared epitop of the PBP2 antigens. The importance of such a kit is based on the need to rapidly identify the drug resistant bacterial strains, as there is a different life threatening situation and different treatment for each type of pathogen.

The invention claimed is:

1. A method for amplification of the detection of a target molecule in a sample comprising:
   a. obtaining at least one binding agent capable of binding to said target molecule, wherein said at least one binding agent is bound to a matrix;
   b. incubating said at least one binding agent which is bound to the matrix with a blocking agent, thereby blocking free active groups on the matrix, wherein said active groups are primary $NH_2$ or COOH groups;
   c. incubating said at least one binding agent which is bound to the matrix with the sample under conditions allowing the binding of the binding agent to the target molecule; thereby forming a matrix-binding agent-target molecule complex;
   d. contacting the matrix-binding agent-target molecule complex formed in step (c) with a polymer associated with a member of an affinity couple, wherein said polymer is non-specific toward the target molecule and further comprises reactive groups, and wherein said reactive groups are reactive with primary $NH_2$ or COOH groups; thereby forming a matrix-binding agent-target molecule-polymer complex; and
   e. contacting said matrix-binding agent-target molecule-polymer complex with a complementary member of said member of an affinity couple, wherein said complementary member is associated with a detectable moiety, wherein the amount of said detectable moiety is indicative of the presence of said target molecule in the sample, wherein said target molecule is a viral antigen, a cancer marker or a soluble antigen selected from the group consisting of soluble cancer markers, inflammation-associated markers, hormones, cytokines, drugs, viral derived soluble molecules, bacterial derived soluble molecules and fungal derived soluble molecules.

2. A method according to claim 1, wherein said binding agent is an aptamer, an antibody, a receptor ligand or a molecular imprinted polymer.

3. A method according to claim 2, wherein said binding agent is an aptamer.

4. A method according to claim 3, wherein said aptamer comprises reactive groups and said matrix is pre-coated with a protein, and wherein said aptamer is bound to the matrix, thereby forming an aptamer-matrix complex.

5. A method according to claim 1, wherein said blocking agent is selected from a group consisting of dimethyl pimelimidate (DMP), citraconic anhydride, sulfo-NHS-Acetate, glutaraldehyde, photo reactive groups, N-acetylcysteine and N, N'-Methanetetraylbis(2-propanamine) (DIPCDI).

6. A method according to claim 1, wherein said member of an affinity couple associated with the polymer is biotin.

7. A method according to claim 1, wherein said polymer is a nucleic acid molecule.

8. A method according to claim 1, wherein said reactive group is a succinimidyl ester group or Tosyl.

9. A method according to claim 1, wherein said target molecule comprises a primary $NH_2$ or COOH group.

10. A method according to claim 7, wherein said nucleic acid molecule is a single stranded nucleic acid forming a complex with biotin during a branched nucleic acid process or as a pre-prepared branch unit.

11. A method according to claim 1, wherein said complementary member of said member of an affinity couple is a biotin-binding protein.

12. A method according to claim 1, wherein said detectable moiety is an enzyme capable of catalyzing a reaction producing a detectable signal and a suitable substrate for said enzyme, wherein said enzyme is Alkaline Phosphatase (AP) or Horse Radish Peroxidase (HRP).

13. A method for the diagnosis of a pathological condition in a subject comprising using a detection method in accordance with claim 1, wherein said target molecule is a target molecule associated with the pathological condition and wherein the amount of said detectable moiety is indicative of the presence of a pathological condition in the subject, and wherein said pathological condition is cancer, an autoimmune disease, or a viral, bacterial or fungal infection.

14. A method for monitoring the efficiency of a therapeutic regimen in a subject suffering from a pathological condition comprising using a detection method in accordance with claim 1, wherein said target molecule is an antigen associated with the pathological condition and wherein the amount of said detectable moiety is indicative of the level of the pathological condition and thereby of the efficiency of the therapeutic regimen in the subject, and wherein said pathological condition is cancer, an autoimmune disease, or a viral, bacterial or fungal infection.

15. The method of claim 1, wherein the at least one binding agent used for binding to the target molecule is a single binding agent.

\* \* \* \* \*

SEQUENCE LISTING

```
<160> NUMBER OF SEQ ID NOS: 13

<210> SEQ ID NO 1
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Universal T7 RNA polymerase

<400> SEQUENCE: 1
taatacgact cactataggg                                              20

<210> SEQ ID NO 2
<211> LENGTH: 25
<212> TYPE: DNA
<213> ORGANISM: Hepatitis B virus

<400> SEQUENCE: 2
cctctgccga tccatactgc ggaac                                        25

<210> SEQ ID NO 3
<211> LENGTH: 29
<212> TYPE: DNA
<213> ORGANISM: Hepatitis B virus

<400> SEQUENCE: 3
ggaggctgta ggcataaatt ggtctgcgc                                    29

<210> SEQ ID NO 4
<211> LENGTH: 20
<212> TYPE: DNA
<213> ORGANISM: Artificial Sequence
<220> FEATURE:
<223> OTHER INFORMATION: Synthetic
<220> FEATURE:
```

<221> NAME/KEY: misc_feature
<223> OTHER INFORMATION: Universal SP6 RNA polymerase

<400> SEQUENCE: 4
atttaggtga cactatagaa                                             20

<210> SEQ ID NO 5
<211> LENGTH: 19
<212> TYPE: DNA
<213> ORGANISM: Hepatitis B virus

<400> SEQUENCE: 5
atgcgctgat ggcctatgg                                              19

<210> SEQ ID NO 6
<211> LENGTH: 39
<212> TYPE: DNA
<213> ORGANISM: Hepatitis B virus

<400> SEQUENCE: 6
cccgagattg agatcttctg cgacgcggcg attgagacc                        39

<210> SEQ ID NO 7
<211> LENGTH: 46
<212> TYPE: DNA
<213> ORGANISM: Homo sapiens

<400> SEQUENCE: 7
gcgatactcc acaggctacg gcacgtagag catcaccatg atcctg                46

<210> SEQ ID NO 8
<211> LENGTH: 46
<212> TYPE: DNA
<213> ORGANISM: Homo sapiens

<400> SEQUENCE: 8
gcgatactcc acagctgacg gcacggtaag catcaccatg atgtcc                46

<210> SEQ ID NO 9
<211> LENGTH: 51
<212> TYPE: DNA
<213> ORGANISM: Homo sapiens

<400> SEQUENCE: 9
gcagttactc agggcacttg caagcaattg tggtcccaat gggctgagta t          51

<210> SEQ ID NO 10
<211> LENGTH: 40
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: cytomegalo virus

<400> SEQUENCE: 10
ttacggtcac cttacccctg ggtgtgctct tcccggtggg                       40

<210> SEQ ID NO 11
<211> LENGTH: 46
<212> TYPE: DNA
<213> ORGANISM: Homo sapiens

<400> SEQUENCE: 11

```
gcgatactcc acagctgacg gcacggtaag catcaccatg atgtcc                    46

<210> SEQ ID NO 12
<211> LENGTH: 45
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<223> OTHER INFORMATION: Listeria

<400> SEQUENCE: 12
atcgatgatc tggtcgccgt aacactaccc acatatacga ccagg                    45

<210> SEQ ID NO 13
<211> LENGTH: 47
<212> TYPE: DNA
<213> ORGANISM: Artificial Sequence
<220> FEATURE:
<223> OTHER INFORMATION: synthetic
<220> FEATURE:
<221> NAME/KEY: misc_feature
<223> OTHER INFORMATION: bacteria

<400> SEQUENCE: 13
atccatgggg cggagatgag ggggaggagg gcgggtaccc ggttgat                   47
```